US006383471B1

(12) United States Patent
Chen et al.

(10) Patent No.: US 6,383,471 B1
(45) Date of Patent: May 7, 2002

(54) COMPOSITIONS AND METHODS FOR IMPROVED DELIVERY OF IONIZABLE HYDROPHOBIC THERAPEUTIC AGENTS

(75) Inventors: Feng-Jing Chen; Mahesh V. Patel, both of Salt Lake City, UT (US)

(73) Assignee: Lipocine, Inc., Salt Lake City, UT (US)

( * ) Notice: Subject to any disclaimer, the term of this patent is extended or adjusted under 35 U.S.C. 154(b) by 0 days.

(21) Appl. No.: 09/287,043

(22) Filed: Apr. 6, 1999

(51) Int. Cl.$^7$ .................................................. A61K 9/12
(52) U.S. Cl. .......................... 424/45; 424/401; 424/46; 424/451; 424/436; 514/944
(58) Field of Search ........................... 424/401, 45, 46, 424/451, 436; 514/944

(56) References Cited

U.S. PATENT DOCUMENTS

| | | |
|---|---|---|
| 4,388,307 A | 6/1983 | Cavanak ...................... 424/177 |
| 4,572,915 A | 2/1986 | Crooks ........................ 514/458 |
| 4,713,246 A | 12/1987 | Begum et al. ............... 424/455 |
| 4,719,239 A | 1/1988 | Muller et al. ............... 514/785 |
| 4,727,109 A | 2/1988 | Schmidt et al. ............. 424/455 |
| 4,731,384 A | 3/1988 | Dell et al. ................... 514/658 |
| 4,944,949 A | 7/1990 | Story et al. ................. 424/451 |
| 5,071,643 A | 12/1991 | Yu et al. ...................... 514/570 |
| 5,145,684 A | 9/1992 | Liversidge et al. ......... 424/489 |
| 5,244,925 A | 9/1993 | Wretlind et al. ............ 514/777 |
| 5,300,529 A | 4/1994 | Narayanan ................... 514/788 |
| 5,342,625 A | 8/1994 | Hauer et al. ................ 424/455 |
| 5,360,615 A | 11/1994 | Yu et al. ...................... 424/455 |
| 5,364,632 A | 11/1994 | Benita et al. ............... 424/450 |
| 5,376,688 A | 12/1994 | Morton et al. .............. 514/786 |
| 5,468,502 A | 11/1995 | Argiriadi et al. ........... 424/456 |
| 5,532,002 A | 7/1996 | Story .......................... 424/456 |
| 5,589,455 A | 12/1996 | Woo ............................. 514/11 |
| 5,614,491 A | 3/1997 | Walch et al. ................ 514/11 |
| 5,616,330 A | 4/1997 | Kaufman et al. ........... 424/400 |
| 5,639,474 A | 6/1997 | Woo ............................ 424/452 |
| 5,639,724 A | 6/1997 | Cavanak ...................... 514/11 |
| 5,645,856 A | 7/1997 | Lacy et al. .................. 424/450 |
| 5,652,212 A | 7/1997 | Cavanak et al. ............ 514/11 |
| 5,653,987 A | 8/1997 | Modi et al. .................. 424/400 |
| 5,726,181 A | 3/1998 | Hausheer et al. ........... 514/283 |
| 5,731,355 A | 3/1998 | Jones et al. ................. 514/731 |
| 5,741,822 A | 4/1998 | Yesair ......................... 514/784 |
| 5,747,066 A | 5/1998 | Pittrof et al. ............... 424/450 |
| 5,766,629 A | 6/1998 | Cho et al. ................... 424/455 |
| 5,773,029 A | 6/1998 | Chiesi et al. ............... 424/488 |
| 5,858,401 A | 1/1999 | Bhalani et al. ............. 424/450 |

OTHER PUBLICATIONS

Alvarez, F. J. and Stella, V. J., "The Role of Calcium Ions and Bile Salts on the Pancreatic Lipase–Catalyzed Hydrolysis of Triglyceride Emulsions Stabilized with Lecithin", *Pharmaceutical Research*, 6(6), 449–457 (1989).
Bates, T. R. and Sequeira, J. A., "Bioavailability of Micronized Griseofulvin from Corn Oil–in–Water Emulsion, Aqueous Suspension, and Commercial Tablet Dosage Forms in Humans", *Journal of Pharmaceutical Sciences*, 64(5), 793–797 (1975).

Charman, W. N., Porter, C.J.H., Mithani, S., and Bressman, J.B., "Physicochemical and Physiological Mechanisms for the Effects of Food on Drug Absorption: The Role of Lipids and pH", *Journal of Pharmceutical Sciences*, 86(3), 269–282 (1997).
Gennaro, A. R., *Remington's Pharmaceutical Sciences*, Chapter 20, 293–300 (1985).
Hörter, D. and Dressman, J.B., "Influence of Physicochemical Properties on Dissolution of Drugs in the Gastrointestinal Tract", *Advanced Drug Delivery Reviews* 25, 3–14 (1997).
Humberstone, A. J. and Charman, W. N. "Lipid–based Vehicles for the Oral Delivery of Poorly Water Soluble Drugs", *Advanced Drug Delivery Reviews*, 103–128 (1997).
Hutchison, K., "Digestible Emulsions and Microemulsions for Optimum Oral Delivery of Hydrophobic Drugs", *Journées Galéniques*, 67–74, (1994).
Johnson, L. R., "Gastrointestinal Physiology", Department of Physiology, University of Texas Medical School, Houston, Texas, 25–26, 93, 106, 133–134, 136–137 (1997).
MacGregor, K. J. et al., "Influence of Lipolysis on Drug Absorption From the Gastro–intestinal Tract", *Advanced Drug Delivery Reviews* 25, 33–46 (1997).
Pouton, C. W., "Formulation of Self–Emulsifying Drug Delivery Systems", *Advanced Drug Delivery Reviews* 25, 47–58 (1997).
Reymond, J. and Sucker, H., "In Vitro Model for Ciclosporin Intestinal Absorption in Lipid Vehicles", *Pharmaceutical Research*, 5(10), 677–679.
Tarr, D. T. and Yalkowsky, S. H. "Enhanced Intestinal Absorption of Cyclosporine in Rats Through the Reduction of Emulsion Droplet Size", *Pharmaceutical Research*, 6(1), 40–43 (1989).
Wilson, C. G., O'Mahony, B., "The Behaviour of Fats and Oils in the Upper G.I. Tract", *Bulletin Technique Gattefossé*, No. 90, 13–18 (1997).
Winne, D., "Dependence of Intestinal Absorption in Vivo on the Unstirred Layer", *Archives of Pharmacology*, 304, 175–181 (1978).
Zhi, J., Rakhit, A., and Patel, I. H., "Effects of Dietary Fat on Drug Absorption", *Clinical Pharmacology and Therapeutics*, 58(5), 487–491 (1995).

*Primary Examiner*—Raj Bawa
(74) *Attorney, Agent, or Firm*—Dianne E. Reed; Reed & Associates

(57) ABSTRACT

The present invention is directed to a pharmaceutical composition including a hydrophobic therapeutic agent having at least one ionizable functional group, and a carrier. The carrier includes an ionizing agent capable of ionizing the functional group, a surfactant, and optionally solubilizers, triglycerides, and neutralizing agents. The invention further relates to a method of preparing such compositions by providing a composition of an ionizable hydrophobic therapeutic agent, an ionizing agent, and a surfactant, and neutralizing a portion of the ionizing agent with a neutralizing agent. The compositions of the invention are particularly suitable for use in oral dosage forms.

114 Claims, No Drawings

COMPOSITIONS AND METHODS FOR IMPROVED DELIVERY OF IONIZABLE HYDROPHOBIC THERAPEUTIC AGENTS

FIELD OF THE INVENTION

The present invention relates to drug delivery systems, and in particular to pharmaceutical compositions for the improved delivery of ionizable hydrophobic compounds and methods therefor.

BACKGROUND

Hydrophobic therapeutic agents, i.e., therapeutic compounds having poor solubility in aqueous solution, present difficult problems in formulating such compounds for effective administration to patients. A well-designed formulation must, at a minimum, be capable of presenting a therapeutically effective amount of the hydrophobic compound to the desired absorption site, in an absorbable form. Even this minimal functionality is difficult to achieve when delivery of the hydrophobic therapeutic agent requires interaction with aqueous physiological environments, such as gastric fluids and intestinal fluids. Pharmaceutical compositions for delivery of such hydrophobic therapeutic agents must carry the hydrophobic compound through the aqueous environment, while maintaining the hydrophobic compound in an absorbable form, and avoiding the use of physiologically harmful solvents or excipients.

A number of approaches to formulating hydrophobic therapeutic agents for oral or parenteral delivery are known. Such approaches include, for example, formulations in which the hydrophobic therapeutic agent is present in an oil-in-water emulsion, a microemulsion, or a solution of micelles, liposomes, or other multi-lamellar carrier particles. While such approaches may be appropriate for some ionizable as well as non-ionizable hydrophobic therapeutic agents, they fail to take advantage of the unique acid-base chemical properties, and associated solubility properties, of ionizable compounds.

In particular, unlike non-ionizable hydrophobic therapeutic agents, ionizable hydrophobic therapeutic agents can be rendered soluble in aqueous solution if the pH of the solution is adjusted to ionize the therapeutic agent. Such an approach is well known in the art. For example, U.S. Pat. No. 5,773,029 is directed to a pharmaceutical composition of an acidic drug, wherein the solubility of the acidic drug is enhanced by simultaneous salt formation with an organic or inorganic base and complexation with a cyclodextrin. The resultant drug/cyclodextrin/base complexes reportedly are readily soluble in water in high concentrations.

U.S. Pat. No. 5,360,615 discloses a pharmaceutical carrier system for an acidic, basic or amphoteric pharmaceutical agent in which the pharmaceutical agent is partially ionized by an acid or base in a polyethylene glycol-based solvent system. The pharmaceutical agent reportedly shows enhanced solubility in the partially ionized form. The reference also discloses that addition of glycerin, propylene glycol and/or polyvinylpyrrolidone further enhances the solubility of the pharmaceutical agent in the polyethylene glycol base. However, the invention is limited to polyethylene glycol-based solvent systems and a narrow range of ionizing agent concentration, and there is no disclosure of other solvent systems. Thus, its utility is severely limited.

Similarly, U.S. Pat. No. 5,376,688 discloses a pharmaceutical solution of an acidic, basic or amphoteric pharmaceutical agent. The solution includes a pharmaceutical agent, an ionizing species, and a solvent system. The solvent system can be diethylene glycol monoethyl ether, glycerol caprylate/caprate, polyglycerol oleate, alpha-hydro-w-hydroxypoly(oxyethylene)-poly(oxypropylene)-poly (oxyethylene) block copolymers, or mixtures of those components. The solvent system can also be a mixture of polyethylene glycol and a polyoxyethylene sorbitan ester. Optional components include water, glycerin, propylene glycol, and polyvinylpyrrolidone. However, the invention is limited to these particular compounds and a narrow range of ionizing agent concentration, rendering its utility severely limited. Moreover, some of the solvent system components show poor or questionable biocompatibility, and thus would be impractical for drug delivery to a patient.

A further problem with conventional approaches to solubilizing ionizable hydrophobic therapeutic agents is the difficulty in maintaining the solubilized therapeutic agent in solubilized form. Thus, for example, while ionizing an acidic therapeutic agent with a base may increase its solubility, the therapeutic agent is prone to precipitation in the gastrointestinal tract due to the acidic pH conditions encountered upon administration to a patient, and the approximately 10 to 100-fold dilution expected in gastrointestinal or intestinal fluids. This precipitation is particularly disadvantageous, since the precipitated therapeutic agent is essentially unavailable for absorption, leading to difficulties in controlling dosages, and a need to administer large doses of the therapeutic agent to ensure that a therapeutically effective amount reaches the absorption site in a bioavailable form. Such difficulties necessarily result in increased costs, and compromised patient safety and therapeutic effectiveness.

Thus, there is a need for versatile and effective pharmaceutical compositions that overcome these deficiencies in the prior art.

SUMMARY OF THE INVENTION

It is therefore an object of the present invention to provide pharmaceutical compositions capable of solubilizing therapeutically effective amounts of ionizable hydrophobic therapeutic agents.

It is another object of the invention to provide pharmaceutical compositions capable of maintaining a solubilized ionizable hydrophobic therapeutic agent in solubilized form upon administration to a patient.

It is another object of the invention to provide pharmaceutical compositions of ionizable hydrophobic therapeutic agents with improved delivery of the therapeutic agent to the absorption site.

It is a further object of the invention to provide improved methods of preparing pharmaceutical compositions of ionizable hydrophobic therapeutic agents.

It is still another object of the invention to provide methods of treating an animal with pharmaceutical compositions of ionizable hydrophobic therapeutic agents.

In accordance with these and other objects and features, the present invention provides pharmaceutical compositions and methods for improved delivery of ionizable hydrophobic therapeutic agents.

In one embodiment, the invention is directed to a pharmaceutical composition including an ionizable hydrophobic therapeutic agent and a carrier. The carrier includes an ionizing agent to ionize the therapeutic agent, and a surfactant. Optionally, the carrier also includes solubilizers, triglycerides and neutralizing agents.

In another embodiment, the invention is directed to a pharmaceutical composition including a hydrophobic therapeutic agent having at least one ionizable functional group, and a carrier. The carrier includes an ionizing agent capable of ionizing the functional group, a surfactant, and a triglyceride.

In another embodiment, the invention is directed to a pharmaceutical composition including a hydrophobic therapeutic agent having at least one ionizable functional group and a carrier, wherein the carrier includes an ionizing agent capable of ionizing the ionizable functional group and present in a pre-reaction amount of greater than about 1.5 mole equivalents per mole of ionizable functional group, and a surfactant. In a further aspect of this embodiment, the composition further includes a neutralizing agent capable of neutralizing a portion of the ionizing agent.

In another embodiment, the invention is directed to a pharmaceutical composition including a hydrophobic therapeutic agent having at least one ionizable functional group, and a carrier, wherein the carrier includes an ionizing agent capable of ionizing the ionizable functional group, a surfactant, and a solubilizer present in an amount of greater than about 10% by weight, based on the total weight of the composition. In this embodiment, the surfactant includes at least one compound from the group consisting of alkylglucosides; alkylmaltosides; alkylthioglucosides; lauryl macrogolglycerides; polyoxyethylene alkyl ethers; fatty acids; lower alcohol fatty acid esters; polyoxyethylene alkylphenols; polyethylene glycol fatty acids esters; polypropylene glycol fatty acid esters; glycerol fatty acid esters; acetylated glycerol fatty acid esters; polyethylene glycol glycerol fatty acid esters; polyglyceryl fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, vegetable oils, hydrogenated vegetable oils, and sterols; sugar esters; sugar ethers; sucroglycerides; fatty acid salts; bile salts; phospholipids; phosphoric acid esters; carboxylates; sulfates; and sulfonates.

In another embodiment, the present invention is directed to a pharmaceutical composition including a hydrophobic therapeutic agent having at least one ionizable functional group and a carrier, wherein the carrier includes an ionizing agent capable of ionizing the ionizable functional group, a surfactant, and a solubilizer. In this embodiment, the surfactant includes at least one compound selected from the group consisting of alkylglucosides; alkylmaltosides; alkylthioglucosides; lauryl macrogolglycerides; fatty acids; lower alcohol fatty acid esters; polyoxyethylene alkylphenols; polyethylene glycol fatty acids esters; polypropylene glycol fatty acid esters; glycerol fatty acid esters; acetylated glycerol fatty acid esters; polyethylene glycol glycerol fatty acid esters; polyglyceryl fatty acid esters; polyoxyethylene sorbitan fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, vegetable oils, hydrogenated vegetable oils, and sterols; sugar esters; sugar ethers; sucroglycerides; fatty acid salts; bile salts; phospholipids; phosphoric acid esters; carboxylates; sulfates; and sulfonates.

The solubilizer in this embodiment includes at least one compound selected from the group consisting of alcohols, polyols, amides, esters, and propylene glycol ethers, the alcohol or polyol being selected from the group consisting of ethanol, isopropanol, butanol, benzyl alcohol, ethylene glycol, propylene glycol, butanediols and isomers thereof, glycerol, pentaerythritol, sorbitol, mannitol, dimethyl isosorbide, polypropylene glycol, polyvinylalcohol, hydroxypropyl methylcellulose and other cellulose derivatives, maltodextrins, and cyclodextrins and cyclodextrin derivatives.

In another embodiment, the present invention provides a method of preparing a pharmaceutical composition of an ionizable hydrophobic therapeutic agent. In this embodiment, the method includes the steps of: providing a pharmaceutical composition having an ionizable hydrophobic therapeutic agent and a carrier which includes an ionizing agent and a surfactant; and providing a neutralizing agent to neutralize at least a portion of the ionizing agent.

In another embodiment, the present invention provides a method of treating an animal with an ionizable hydrophobic therapeutic agent. The method includes the steps of providing a pharmaceutical composition having an ionizable hydrophobic therapeutic agent and a carrier which includes an ionizing agent and a surfactant; and administering the pharmaceutical composition to an animal.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The present invention overcomes the problems described above characteristic of conventional formulations, by providing pharmaceutical compositions including an ionizable hydrophobic therapeutic agent and a carrier. The carrier includes a surfactant, and an ionizing agent capable of ionizing the ionizable hydrophobic therapeutic agent. Optional components include one or more additional surfactants, solubilizers, triglycerides, neutralizing agents, and various additives. The carrier is able to solubilize the ionizable hydrophobic therapeutic agent and maintain the therapeutic agent in solubilized form for improved delivery to the absorption site The invention also encompasses various dosage forms of the pharmaceutical composition.

The present invention further provides a method of solubilizing ionizable hydrophobic therapeutic agents for improved performance in pharmaceutical compositions. The method includes the steps of providing a pharmaceutical composition as described above, and providing a neutralizing agent to neutralize a portion of the ionizing agent.

1. Ionizable Hydrophobic Therapeutic Agents

Ionizable hydrophobic therapeutic agents suitable for use in the pharmaceutical compositions of the present invention are not particularly limited, as the carrier is surprisingly capable of solubilizing and delivering a wide variety of ionizable hydrophobic therapeutic agents. Ionizable hydrophobic therapeutic agents are compounds with little or no water solubility at neutral pH. Intrinsic water solubilities (i.e., water solubility of the unionized form) for the ionizable hydrophobic therapeutic agents usable in the present invention are less than about 1% by weight, and typically less than about 0.1% or 0.01% by weight. Such therapeutic agents can be any agents having therapeutic or other value when administered to an animal, particularly to a mammal, such as drugs, nutrients, and cosmetics (cosmeceuticals). It should be understood that while the invention is described with particular reference to its value in oral dosage form, the invention is not so limited. Thus, ionizable hydrophobic drugs, nutrients or cosmetics which derive their therapeutic or other value from, for example, topical or transdermal administration, are still considered to be suitable for use in the present invention.

It is a particular feature of the present invention that a wide variety of therapeutic agents can be effectively incorporated in and delivered by the present pharmaceutical compositions. The essential feature of a suitable therapeutic agent is the presence of at least one ionizable functional group. Ionizable functional groups can be acidic groups, or basic groups, with "acidic" and "basic" referring to acidic or basic behavior in a Brønsted-Lowry or Lewis acid/base sense. Acidic functional groups are those groups that can be deprotonated by a suitable base to yield the corresponding anionic group (the conjugate base), or groups that can accept an electron pair. Basic functional groups are those groups that can be protonated by a suitable acid to yield the corresponding cationic group (the conjugate acid), or can donate an electron pair. It should be appreciated that the suitability of a therapeutic agent for use in the methods and compositions of the present invention is not determined by its therapeutic class, but is instead determined by the acid-base properties of its acidic or basic functional groups.

The terms "acid" and "base" as used herein refer to the ability of a functional group to act as a Brønsted-Lowry acid or Lewis acid, or as a Brønsted-Lowry base or Lewis base, in the presence of an appropriate ionizing agent. For simplicity, the acidic and basic properties of functional groups, ionizing agents, and neutralizing agents are described herein with particular reference to Brønsted-Lowry properties, but the corresponding Lewis acid/base properties are also included within the scope of these terms.

This usage should be contrasted with the terminology typically used in describing whether a compound is "acidic" or "basic" based on the $pK_a$ of the compound in deionized water. For example, the equivalent $pK_a$ of a functional group need not be less than 7 to be considered "acidic", since even functional groups with a large $pK_a$ can be "acidic" if they can be deprotonated by a strong base. Similarly, a functional group with an equivalent $pK_a$ of less than 7 may still be considered "basic" if it can be protonated by a stronger acid. Thus, it is the ability of a particular functional group to be ionized (protonated or deprotonated) by a suitable ionizing agent (acid or base) that determines whether a functional group is acidic or basic, rather than the particular $pK_a$ associated with that group or with the compound as a whole.

As a specific example, itraconazole is a hydrophobic therapeutic agent having a $pK_a$ of 3.7, and a $pK_b$ of 10.3. Thus, itraconazole can be protonated by an acid having a $pK_a$ less than 3.7, or deprotonated by a base having a $pK_b$ less than 10.3.

Suitable therapeutic agents contain at least one ionizable functional group. Of course, many suitable therapeutic agents contain a plurality of such groups, and a single therapeutic agent may contain one or more acidic functional groups as well as one or more basic functional groups. Such therapeutic agents are also within tile scope of the present invention.

Acidic functional groups include, but are not limited to, carboxylic acids, imidazolidinediones, thiazolidinediones, pyrimidinetriones, hydroxyheteroaromatics, phenols, phosphoric acids, sulfuric acids, sulfonic acids, sulfonamides, aminosulfones, sulfonylureas, tetrazoles and thiols.

In order to avoid particularly cumbersome terminology, the functional groups, whether acidic or basic, are referred to by naming the corresponding free compound. For example, referring to a functional group, the term "aminosulfone" is used, rather than the more technically precise term "aminosulfonyl". This usage is common in the art, and is well understood by one skilled in the art.

Basic functional groups include, but are not limited to, aliphatic amines, aromatic amines, C-substituted aromatic amines, N-substituted aromatic amines, heterocyclic amines, C-substituted heterocyclic amines and N-substituted heterocyclic amines.

Examples of aromatic amines and substituted aromatic amines include, but are not limited to, aniline, N-methylaniline and p-toluidine.

Examples of heterocyclic and substituted heterocyclic amines include, but are not limited to, pyrrole, pyrazole, imidazole, indole, pyridine, pyridazine, pyrimidine, quinoline, piperidine, pyrrolidine, morpholine, thiazole, purine and triazole.

Specific examples of suitable therapeutic agents having at least one ionizable acidic functional group include, but are not limited to: acetazolamide, acetohexamide, acrivastine, alatrofloxacin, albuterol, alclofenac, aloxiprin, alprostadil, amodiaquine, amphotericin, amylobarbital, aspirin, atorvastatin, atovaquone, baclofen, barbital, benazepril, bezafibrate, bromfenac, bumetanide, butobarbital, candesartan, capsaicin, captopril, cefazolin, celecoxib, cephadrine, cephalexin, cerivastatin, cetrizine, chlorambucil, chlorothiazide, chlorpropamide, chlorthalidone, cinoxacin, ciprofloxacin, clinofibrate, cloxacillin, cromoglicate, cromolyn, dantrolene, dichlorophen, diclofenac, dicloxacillin, dicumarol, diflunisal, dimenhydrinate, divalproex, docusate, dronabinol, enoximone, enalapril, enoxacin, enrofloxacin, epalrestat, eposartan, essential fatty acids, estramustine, ethacrynic acid, ethotoin, etodolac, etoposide, fenbufen, fenoprofen, fexofenadine, fluconazole, flurbiprofen, fluvastatin, fosinopril, fosphenytoin, fumagillin, furosemide, gabapentin, gemfibrozil, gliclazide, glipizide, glybenclamide, glyburide, glimepiride, grepafloxacin, ibufenac, ibuprofen, imipenem, indomethacin, irbesartan, isotretinoin, ketoprofen, ketorolac, lamotrigine, levofloxacin, levothyroxine, lisinopril, lomefloxacin, losartan, lovastatin, meclofenamic acid, mefenamic acid, mesalamine, methotrexate, metolazone, montelukast, nalidixic acid, naproxen, natamycin, nimesulide, nitrofurantoin, non-essential fatty acids, norfloxacin, nystatin, ofloxacin, oxacillin, oxaprozin, oxyphenbutazone, penicillins, pentobarbital, perfloxacin, phenobarbital, phenytoin, pioglitazone, piroxicam, pramipexol, pranlukast, pravastatin, probenecid, probucol, propofol, propylthiouracil, quinapril, rabeprazole, repaglinide, rifampin, rifapentine, sparfloxacin, sulfabenzamide, sulfacetamide, sulfadiazine, sulfadoxine, sulfamerazine, sulfamethoxazole, sulfafurazole, sulfapyridine, sulfasalazine, sulindac, sulphasalazine, sulthiame, telmisartan, teniposide, terbutaline, tetrahydrocannabinol, tirofiban, tolazamide, tolbutamide, tolcapone, tolmetin, tretinoin, troglitazone, trovafloxacin, undecenoic acid, ursodeoxycholic acid, valproic acid, valsartan, vancomycin, verteporfin, vigabatrin, vitamin K-S (II) and zafirlukast.

Among the above-listed hydrophobic therapeutic agents having at least one acidic functional group, preferred hydrophobic therapeutic agents are: acetohexamide, acrivastine, alatrofloxacin, albuterol, alclofenac, amodiaquine, amphotericin, aspirin, atorvastatin, atovaquone, baclofen, benazepril, bezafibrate, bromfenac, butobarbital, candesartan, capsaicin, captopril, celecoxib, cerivastatin, cetrizine, chlorambucil, chlorpropamide, chlorthalidone, clinofibrate, cinoxacin, ciprofloxacin, clinofibrate, cloxacillin, cromoglicate, cromolyn, dantrolene, diclofenac, dicumarol, divalproex, docusate, dronabinol, enalapril, enoxacin, eposartan, etodolac, etoposide, fenbufen, fenoprofen, fexofenadine, fluconazole, flurbiprofen, fluvastatin, fosphenytoin, fumagillin, gabapentin, gemfibrozil, gliclazide, glipizide, glyburide, glimepiride, grepafloxacin, ibufenac, ibuprofen, imipenem, indomethacin, irbesartan, isotretinoin, ketoprofen, ketorolac, lamotrigine, levofloxacin, levothyroxine, lisinopril, lomefloxacin, losartan, lovastatin, mesalamine, methotrexate, montelukast, naproxen, nimesulide, non-essential fatty acids, norfloxacin, ofloxacin, oxaprozin, phenytoin, pioglitazone, piroxicam, pramipexol, pravastatin, probucol, propofol, rabeprazole, repaglinide, rifampin, rifapentine, sparfloxacin, sulfadiazine, sulfamethoxazole, sulfasalazine, sulindac, sulphasalazine, telmisartan, teniposide, terbutaline, tetrahydrocannabinol, tirofiban, tolazamide, tolbutamide, tolcapone, tolmetin, tretinoin, troglitazone, trovafloxacin, undecenoic acid, valproic acid, valsartan, vancomycin, verteporfin, vigabatrin, vitamin K-S (II) and zafirlukast.

Among the preferred hydrophobic therapeutic agents having at least one ionizable acidic functional group, the more preferred hydrophobic therapeutic agents are: acrivastine, alatrofloxacin, albuterol, aldlofenac, aspirin, atorvastatin, atovaquone, baclofen, benazepril, bezafibrate, bromfenac, butobarbital, celecoxib, cerivastatin, cetrizine, chlorpropamide, ciprofloxacin, cromoglicate, cromolyn, dantrolene, diclofenac, dicumarol, divalproex, dronabinol, enoxacin, etodolac, etoposide, fenoprofen, fexofenadine, fluconazole, flurbiprofen, fluvastatin, fosphenytoin, gemfibrozil, glipizide, glyburide, glimepiride, grepafloxacin, ibufenac, ibuprofen, isotretinoin, ketoprofen, ketorolac, lamotrigine, levofloxacin, levothyroxine, lomefloxacin, lovastatin, methotrexate, montelukast, naproxen, nimesulide, non-essential fatty acids, norfloxacin, ofloxacin, oxaprozin, phenytoin, pioglitazone, piroxicam, pravastatin, probucol, rabeprazole, repaglinide, rifampin, rifapentine, sulfamethoxazole, sulfasalazine, teniposide, tetrahydrocannabinol, tolcapone, tolmetin, tretinoin, troglitazone, trovafloxacin, valproic acid, vancomycin, vitamin K-S (II) and zafirlukast.

The most preferred hydrophobic therapeutic agents having at least one ionizable acidic functional group are: alclofenac, aspirin, atorvastatin, atovaquone, benazepril, bromfenac, celecoxib, cromoglicate, cromolyn, diclofenac, dronabinol, etodolac, fexofenadine, flurbiprofen, glimepiride, ibufenac, ibuprofen, isotretinoin, ketoprofen, ketorolac, levothyroxine, naproxen, non-essential fatty acids, oxaprozin, phenytoin, pioglitazone, rabeprazole, repaglinide, teniposide, tetrahydrocannabinol, tolmetin, tretinoin, troglitazone, trovafloxacin and vitamin K-S (II).

Specific examples of suitable hydrophobic therapeutic agents having at least one ionizable basic functional group include, but are not limited to: abacavir, acebutolol, acrivastine, alatrofloxacin, albuterol, albendazole, alprazolam, alprenolol, amantadine, amiloride, aminoglutethimide, amiodarone, amitriptyline, amlodipine, amodiaquine, amoxapine, amphetamine, amphotericin, amprenavir, amrinone, amsacrine, astemizole, atenolol, atropine, azathioprine, azelastine, azithromycin, baclofen, benethamine, benidipine, benzhexol, benznidazole, benztropine, biperiden, bisacodyl, bisanthrene, bromazepam, bromocriptine, bromperidol, brompheniramine, brotizolam, bupropion, butenafine, butoconazole, cambendazole, camptothecin, carbinoxamine, cephadrine, cephalexin, cetrizine, cinnarizine, chlorambucil, chlorpheniramine, chlorproguanil, chlordiazepoxide, chlorpromazine, chlorprothixene, chloroquine, cimetidine, ciprofloxacin, cisapride, citalopram, clarithromycin, clemastine, clemizole, clenbuterol, clofazimine, clomiphene, clonazepam, clopidogrel, clozapine, clotiazepam, clotrimazole, codeine, cyclizine, cyproheptadine, dacarbazine, darodipine, decoquinate, delavirdine, demeclo-cycline, dexamphetamine, dexchlorpheniramine, dexfenfluramine, diamorphine, diazepam, diethylpropion, dihydrocodeine, dihydroergotamine, diltiazem, dimenhydrinate, diphenhydramine, diphenoxylate, diphenyl-imidazole, diphenylpyraline, dipyridamole, dirithromycin, disopyramide, dolasetron, domperidone, donepezil, doxazosin, doxycycline, droperidol, econazole, efavirenz, ellipticine, enalapril, enoxacin, enrofloxacin, eperisone, ephedrine, ergotamine, erythromycin, ethambutol, ethionamide, ethopropazine, etoperidone, famotidine, felodipine, fenbendazole, fenfluramine, fenoldopam, fentanyl, fexofenadine, flecainide, flucytosine, flunarizine, flunitrazepam, fluopromazine, fluoxetine, fluphenthixol, fluphenthixol decanoate, fluphenazine, fluphenazine decanoate, flurazepam, flurithromycin, frovatriptan, gabapentin, granisetron, grepafloxacin, guanabenz, halofantrine, haloperidol, hyoscyamine, imipenem, indinavir, irinotecan, isoxazole, isradipine, itraconazole, ketoconazole, ketotifen, labetalol, lamivudine, lanosprazole, leflunomide, levofloxacin, lisinopril, lomefloxacin, loperamide, loratadine, lorazepam, lormetazepam, lysuride, mepacrine, maprotiline, mazindol, mebendazole, meclizine, medazepam, mefloquine, melonicam, meptazinol, mercaptopurine, mesalamine, mesoridazine, metformin, methadone, methaqualone, methylphenidate, methylphenobarbital, methysergide, metoclopramide, metoprolol, metronidazole, mianserin, miconazole, midazolam, miglitol, minoxidil, mitomycins, mitoxantrone, molindone, montelukast, morphine, moxifloxacin, nadolol, nalbuphine, naratriptan, natamycin, nefazodone, nelfinavir, nevirapine, nicardipine, nicotine, nifedipine, nimodipine, nimorazole, nisoldipine, nitrazepam, nitrofurazone, nizatidine, norfloxacin, nortriptyline, nystatin, ofloxacin, olanzapine, omeprazole, ondansetron, omidazole, oxamniquine, oxantel, oxatomide, oxazepam, oxfendazole, oxiconazole, oxprenolol, oxybutynin, oxyphencyclimine, paroxetine, pentazocine, pentoxifylline, perchlorperazine, perfloxacin, perphenazine, phenbenzamine, pheniramine, phenoxybenzamine, phentermine, physostigmine, pimozide, pindolol, pizotifen, pramipexol, pranlukast, praziquantel, prazosin, procarbazine, prochlorperazine, proguanil, propranolol, pseudoephedrine, pyrantel, pyrimethamine, quetiapine, quinidine, quinine, raloxifene, ranitidine, remifentanil, repaglinide, reserpine, ricobendazole, rifabutin, rifampin, rifapentine, rimantadine, risperidone, ritonavir, rizatriptan, ropinirole, rosiglitazone, roxatidine, roxithromycin, salbutamol, saquinavir, selegiline, sertraline, sibutramine, sildenafil, sparfloxacin, spiramycins, stavudine, sulconazole, sulphasalazine, sulpiride, sumatriptan, tacrine, tamoxifen, tamsulosin, temazepam, terazosin, terbinafine, terbutaline, terconazole, terfenadine, tetramisole, thiabendazole, thioguanine, thioridazine, tiagabine, ticlopidine, timolol, tinidazole, tioconazole, tirofiban, tizanidine, tolterodine, topotecan, toremifene, tramadol, trazodone, triamterene, triazolam, trifluoperazine, trimethoprim, trimipramine, tromethamine, tropicamide, trovafloxacin, vancomycin, venlafaxine, vigabatrin, vinblastine, vincristine, vinorelbine, vitamin $K_5$, vitamin $K_6$, vitamin $K_7$, zafirlukast, zolmitriptan, zolpidem and zopiclone.

Among the above-listed hydrophobic therapeutic agents having at least one ionizable basic functional group, preferred hydrophobic therapeutic agents are: abacavir, acebutolol, acrivastine, alatrofloxacin, albendazole, albuterol, alprazolam, amiodarone, amlodipine, amodiaquine, amphetamine, amphotericin, amprenavir, astemizole, atenolol, azathioprine, azelastine, azithromycin, baclofen, benztropine, bisacodyl, bromazepam, bromperidol, brompheniramine, bupropion, butenafine, butoconazole, cambendazole, camptothecin, carbinoxamine, cetrizine, cinnarizine, chlorpheniramine, chlorambucil, chlorpromazine, cimetidine, ciprofloxacin, cisapride, citalopram, clarithromycin, clemastine, clemizole, clomiphene, clonazepam, clopidogrel, clozapine, clotiazepam, clotrimazole, codeine, cyclizine, delavirdine, dexamphetamine, dexchlorpheniramine, diamorphine, diazepam, diethylpropion, dihydrocodeine, dihydroergotamine, diltiazem, diphenhydramine, diphenylimidazole, diphenylpyraline, dipyridamole, dirithromycin, disopyramide, dolasetron, domperidone, donepezil, doxazosin, droperidol, econazole, efavirenz, ellipticine, enalapril, enoxacin, eperisone, ergotamine, famotidine, felodipine, fenfluramine, fenoldopam, fexofenadine, fentanyl, flecainide, flunarizine, fluopromazine, fluoxetine, frovatriptan, gabapentin, granisetron, halofantrine, imipenem, indinavir, irinotecan, isoxazole, isradipine, itraconazole, ketoconazole, ketotifen, labetalol, lamivudine, lanosprazole, leflunomide, levofloxacin, lisinopril, lomefloxacin, loperamide, loratadine, lorazepam, lormetazepam, mazindol, mebendazole, mefloquine, mercaptopurine, mesalamine, metformin, methadone, methaqualone, methylphenidate, methysergide, metoclopramide, metoprolol, metronidazole, miconazole, midazolam, miglitol, minoxidil, mitoxantrone, montelukast, naratriptan, nelfinavir, nevirapine, nicardipine, nicotine, nifedipine, nimodipine, nimorazole, nisoldipine, nizatidine, norfloxacin, ofloxacin, olanzapine, omeprazole, ondansetron, oxamniquine, oxiconazole, paroxetine, perchlorperazine, phenbenzamine, pheniramine, phentermine, physostigmine, pizotifen, pramipexol, prazosin, prochlorperazine, pseudoephedrine, quetiapine, quinidine, raloxifene, ranitidine, remifentanil, repaglinide, rifabutin, rifampin, rifapentine, rimantadine, risperidone, ritonavir, rizatriptan, rosiglitazone, roxatidine, saquinavir, sibutramine, sildenafil, sparfloxacin, stavudine, sulphasalazine, sumatriptan, tacrine, tamoxifen, tamsulosin, terazosin, terbinafine, terbutaline, terconazole, terfenadine, tiagabine, ticlopidine, tinidazole, tioconazole, tirofiban, tizanidine, tolterodine, topotecan, toremifene, tramadol, trazodone, trovafloxacin, vancomycin, venlafaxine, vigabatrin, vinblastine, vincristine, vinorelbine, vitamin $K_5$, vitamin $K_6$, vitamin $K_7$, zafirlukast, zolmitriptan, zolpidem and zopiclone.

Among the preferred hydrophobic therapeutic agents having at least one ionizable basic functional group, more preferred hydrophobic therapeutic agents are: abacavir, acrivastine, alatrofloxacin, albuterol, amiodarone, amlodipine, amphetamine, amprenavir, astemizole, atenolol, azathioprine, azelastine, azithromycin, baclofen, benztropine, bisacodyl, bromazepaam, bromperidol, brompheniramine, bupropion, butenafine, butoconazole, cambendazole, camptothecin, carbinoxamine, cetrizine, cinnarizine, chlorpheniramine, chlorpromazine, cimetidine, ciprofloxacin, cisapride, clarithromycin, clemastine, clemizole, clonazepam, clopidogrel, clotrimazole, codeine, dexchlorpheniramine, dihydrocodeine, dihydroergotamine, diphenhydramine, diphenylimidazole, diphenylpyraline, dirithromycin, dolasetron, domperidone, doxazosin, econazole, efavirenz, ellipticine, enoxacin, eperisone, ergotamine, famotidine, fenoldopam, fentanyl, fexofenadine, flunarizine, fluoxetine, frovatriptan, granisetron, grepafloxacin, halofantrine, indinavir, irinotecan, isradipine, itraconazole, ketoconazole, ketotifen, lamivudine, lanosprazole, leflunomide, levofloxacin, loperamide, loratadine, metformin, methadone, methylphenidate, methysergide, metronidazole, miconazole, midazolam, miglitol, mitoxantrone, montelukast, naratriptan, nelfinavir, nicotine, nifedipine, nimorazole, nizatidine, norfloxacin, ofloxacin, omeprazole, ondansetron, perchlorperazine, phenbenzamine, physostigmine, pizotifen, pseudoephedrine, quetiapine, quinidine, raloxifene, ranitidine, remifentanil, repaglinide, rifabutin, rifampin, rifapentine, rimantadine, ritonavir, rizatriptan, rosiglitazone, roxatidine, saquinavir, sibutramine, sildenafil, stavudine, sumatriptan, tacrine, tamoxifen, tamsulosin, terazosin, terbinafine, tinidazole, tizanidine, tolterodine, topotecan, toremifene, tramadol, trovafloxacin, vancomycin, vinblastine, vincristine, vinorelbine, vitamin $K_5$, vitamin $K_6$, vitamin $K_7$, zafirlukast, zolmitriptan and zolpidem.

The most preferred hydrophobic therapeutic agents having at least one ionizable basic functional group are: amlodipine, astemizole, brompheniramine, bupropion, carbinoxamine, cetrizine, cimetidine, cisapride, clemastine, clemizole, dihydroergotamine, diphenhydramine, diphenylimidazole, diphenylpyraline, domperidone, famotidine, fexofenadine, frovatriptan, granisetron, itraconazole, ketoconazole, ketotifen, lanosprazole, leflunomide, loperamide, loratadine, methysergide, miglitol, montelukast, naratriptan, nizatidine, omeprazole, ondansetron, phenbenzamine, pseudoephedrine, raloxifene, ranitidine, repaglinide, rifabutin, rimantadine, ritonavir, rizatriptan, rosiglitazone, roxatidine, saquinavir, sibutramine, sildenafil, sumatriptan, tamsulosin, terbinafine, tizanidine, tramadol, trovafloxacin, vitamin $K_5$, vitamin $K_6$, vitamin $K_7$, zafirlukast, zolmitriptan and zolpidem.

Also included within the scope of the invention are pharmaceutically equivalent derivatives and/or analogs of the ionizable hydrophobic therapeutic agents. Such equivalents include salts, esters, alkyl and acyl derivatives, liposome-encapsulated derivatives, o/w emulsions of derivatives, and the like.

In particular, salts of ionizable hydrophobic therapeutic agents are suitable for use in the present invention. Salts may be used advantageously for the sake of salt exchange with the acid or base ionizing agent, leading to better salt selection.

It should be appreciated that this listing of ionizable hydrophobic therapeutic agents is merely illustrative. Indeed, a particular feature, and surprising advantage, of the compositions of the present invention is the ability of the present compositions to solubilize and deliver a broad range of ionizable hydrophobic therapeutic agents, regardless of therapeutic class. Of course, mixtures of ionizable hydrophobic therapeutic agents may also be used where desired.

The amount of hydrophobic therapeutic agent to be used depends upon the dosage amount to be delivered. One skilled in the art can determine the appropriate dosage amount, depending upon the specific hydrophobic therapeutic agent to be delivered, the nature of the condition treated, the relative efficacy of the therapeutic agent, and other factors commonly considered. The compositions of the present invention can contain a therapeutically effective amount of the therapeutic agent, up to the amount of therapeutic agent that can be solubilized in the carrier. In addition, if desired the compositions can further contain an additional amount of the hydrophobic therapeutic agent suspended (not solubilized) in the carrier.

2. Ionizing Agents

The ionizing agent can be any pharmaceutically acceptable acid or base capable of protonating or deprotonating the ionizable functional groups of the ionizable hydrophobic therapeutic agent, in a Brønsted-Lowry sense, or capable of accepting or donating an electron pair, in a Lewis sense. For convenience, the ionizing agents are discussed in terms of Brønsted-Lowry properties, although Lewis acids and bases are also suitable ionizing agents.

Ionizing agents that deprotonate the acidic functional groups of the therapeutic agent are pharmaceutically acceptable organic or inorganic bases. Examples of such bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, and the like. Also suitable are bases which are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Preferred cations include sodium, potassium, lithium, magnesium, calcium and ammonium. Ionizing agents that protonate the basic functional groups of the therapeutic agent are pharmaceutically acceptable inorganic or organic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like. Of course, the distinction between inorganic and organic acids is not particularly important, but is provided merely as a convenient and conventional way to classify the acids.

In one embodiment, the ionizing agent is present in an amount sufficient to ionize at least a portion of the ionizable functional groups. In this embodiment, the ionizing agent preferably is present in an amount of at least about 0.1 mole equivalents per mole of ionizable functional groups. The term "mole equivalents" as used herein means the number of moles of ionizing functionality effectively presented by the ionizing agent. Thus, for example, when the ionizing agent is a diprotic acid capable of ionizing two moles of basic functional groups per mole of the diprotic acid, only 0.5 moles of the ionizing agent per mole of ionizable functional groups is necessary to provide 1.0 mole equivalents of ionizing agent.

Whether a particular acid is diprotic or polyprotic for purposes of determining the number of mole equivalents for a given concentration depends upon the basicity of the functional group to be ionized. Thus, for example, phosphoric acid is potentially a tri-protic acid, capable of protonating three moles of functional groups per mole of phosphoric acid, in successive ionization steps:

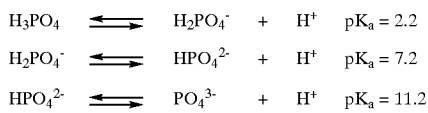

Representing the ionizable basic therapeutic agent as "D", the corresponding ionization reaction is:

Each successive ionization step will only occur, however, if the $pK_a$ of the acid is less than the $pK_a$ of the therapeutic agent. Thus, when the therapeutic agent is, for example, itraconazole, with a $pK_a$ of 3.7, only the first reaction will occur to any appreciable extent. With respect to itraconazole, phosphoric acid behaves as a mono-protic acid, and one mole of phosphoric acid provides one mole equivalent of ionizing agent. Similar considerations apply when the ionizing agent is a base, and the ionizable functional group is acidic.

In one embodiment of the invention, the ionizing agent is present in an amount of at least about 0.1 mole equivalents per mole of ionizable functional group. Preferably, the ionizing agent is present in an amount of at least about 0.2 mole equivalents per mole of ionizable functional group, more preferably at least about 0.5 mole equivalents.

When the pharmaceutical composition is intended for formulation in a dosage form that shows poor compatibility with the ionizing agent, such as a gelatin capsule, the ionizing agent is preferably present in an amount of less than about 1.5 mole equivalents per mole of ionizable functional group, and more preferably less than about 1.0 mole equivalents.

In another embodiment of the invention, the ionizing agent is present in an amount of greater than about 1.0 mole equivalents per mole of ionizable functional group. In a further embodiment of the invention, the ionizing agent is present in an amount of greater than about 1.5 mole equivalents per mole of ionizable functional group.

The use of an excess (i.e., greater than 1.0 mole equivalents or greater than 1.5 mole equivalents) of ionizing agent presents several advantages. Since solubilization of the hydrophobic therapeutic agent depends upon the therapeutic agent being ionized, a higher concentration of ionizing agent provides a greater extent of ionization and thus increased i: solubilization. This increased solubilization is particularly important when the acid or base ionization constants ($K_a$ or $K_b$) of the ionizing agent and the therapeutic agent are similar in magnitude. For example, when the ionization constants are within about an order of magnitude of each other, the ionized and un-ionized forms of the therapeutic agent will be in equilibrium, with a significant amount of the therapeutic agent being present in the unionized form. When the ionization constants differ by about two or more orders of magnitude, an equilibrium is still present, but the amount of non-ionized therapeutic agent will be negligibly small.

A further advantage of using an excess of ionizing agent is in ease of preparation. Higher concentrations of ionizing agent facilitate rapid and complete solubilization, making the preparation of solubilized therapeutic agent easier and more efficient, thereby conserving expensive manufacturing and personnel resources.

In addition, it is believed that higher levels of ionizing agent, when used in the compositions of the present invention, advantageously promote continued solubilization of the therapeutic agent, both for storage of the composition, as well as in the gastrointestinal tract upon administration of the composition to a patient.

Although use of higher levels of ionizing agent in the compositions of the present invention presents several advantages, such higher levels are known to be poorly compatible with conventional gelatin capsule dosage forms. Thus, when the dosage form is a gelatin capsule containing the pharmaceutical compositions of the present invention, it is desirable to use a smaller amount of ionizing agent. In a further embodiment of the invention, a composition of the present invention includes an ionizing agent in an amount of greater than about 1.5 mole equivalents per mole of ionizable functional group, and an amount of a neutralizing agent for the ionization agent present in an amount sufficient to at least partially neutralize the excess ionizing agent. For example, if the ionizing agent is an acid, the neutralizing agent would be a base, and vice versa. The pharmaceutically acceptable acids and bases described herein are suitable for use as the neutralizing agent in this embodiment. Thus, this embodiment provides the advantages of increased solubilization and ease of preparation resulting from a high concentration of ionizing agent, while still preserving good compatibility with conventional gelatin capsules by neutralizing some of the excess ionizing agent.

It should be emphasized that when the dosage form is, for example, a liquid drink, neutralization of excess ionizing agent may be unnecessary, and even large excesses of ionizing agent can be used. One skilled in the art can readily determine the amount of excess ionizing agent that can be used, depending upon the ultimate pH of the solution, the degree of bioacceptability of the ionizing agent, the resultant solution taste, and other factors conventional in the art. By way of illustration only, as shown in the Examples herein, the ionizing agent can be used in an amount of several mole equivalents to tens of mole equivalents or more, per mole of ionizable functional group. These large amounts of ionizing agent can also be used when the ultimate dosage form is a gelatin capsule, or when it is desired for any reason to have a lower ionizing agent concentration, by adding a suitable neutralizing agent, as described above.

It should be understood with respect to all of the embodiments described herein that the concentration of ionizing agent given is the concentration prior to the acid-base reaction, unless otherwise noted. Of course, if the concentration of ionizing agent is, for example, 1.0 mole equivalents per mole of ionizable functional group, upon mixing of the ionizing agent and the ionizable pharmaceutical compound, an acid-base reaction will occur, and such reaction will consume some or all of the ionizing agent. Thus, a given concentration of ionizing agent refers to the pre-reaction concentration, and not to the ultimate concentration of the ionizing agent.

3. Surfactants

The carrier includes at least one surfactant. The surfactant can by hydrophilic, hydrophobic, or a mixture of hydrophilic and hydrophobic surfactants. As is well known in the art, the terms "hydrophilic" and "hydrophobic" are relative teyms. To function as a surfactant, a compound must necessarily include polar or charged hydrophilic moieties as well as non-polar hydrophobic (lipophilic) moieties; i.e., a surfactant compound must be amphiphilic. An empirical parameter commonly used to characterize the relative hydrophilicity and hydrophobicity of non-ionic amphiphilic compounds is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions.

Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10.

It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value (Schott, *J. Pharm. Sciences*, 79(1), 87–88 (1990)). Likewise, for certain polypropylene oxide containing block copolymers (poloxamers, available commercially as PLURONIC® surfactants, BASF Corp.), the HLB values may not accurately reflect the true physical chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or hydrophobicity for use in the present invention, as described herein.

The compositions of the present invention include at least one surfactant. Suitable surfactants can be ionic hydrophilic surfactants, non-ionic hydrophilic surfactants, or hydrophobic surfactants. The surfactant can be any surfactant suitable for use in pharmaceutical compositions. Suitable hydrophilic surfactants can be anionic, cationic, zwitterionic or non-ionic, although non-ionic hydrophilic surfactants are presently preferred. Preferably, the compositions include at least one non-ionic hydrophilic surfactant. Also preferred are mixtures of two or more non-ionic hydrophilic surfactants, as well as mixtures containing at least one non-ionic hydrophilic surfactant and at least one hydrophobic surfactant.

The choice of specific surfactants should be made keeping in mind the particular hydrophobic therapeutic agent to be used in the composition, and the range of polarity appropriate for the chosen therapeutic agent. With these general principles in mind, a very broad range of surfactants is suitable for use in the present invention. Such surfactants can be grouped into the following general chemical classes detailed in the Tables herein. The HLB values given in the Tables below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable.

It should be emphasized that the invention is not limited to the surfactants in the Tables, which show representative, but not exclusive, lists of available surfactants.

3.1. Polyethoxylated Fatty Acids

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful. Among the surfactants of Table 1, preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Examples of polyethoxylated fatty acid monoester surfactants commercially available are shown in Table 1.

TABLE 1

PEG-Fatty Acid Monoester Surfactants

| COMPOUND | COMMERCIAL PRODUCT (Supplier) | HLB |
|---|---|---|
| PEG 4–100 monolaurate | Crodet L series (Croda) | >9 |
| PEG 4–100 monooleate | Crodet O series (Croda) | >8 |
| PEG 4–100 monostearate | Crodet S series (Croda), Myrj Series (Atlas/ICI) | >6 |
| PEG 400 distearate | Cithrol 4DS series (Croda) | >10 |
| PEG 100, 200, 300 monolaurate | Cithrol ML series (Croda) | >10 |
| PEG 100, 200, 300 monooleate | Cithrol MO series (Croda) | >10 |
| PEG 400 dioleate | Cithrol 4D0 series (Croda) | >10 |
| PEG 400–1000 monostearate | Cithrol MS series (Croda) | >10 |
| PEG-1 stearate | Nikkol MYS-1EX (Nikko), Coster K1 (Condea) | 2 |
| PEG-2 stearate | Nikkol MYS-2 (Nikko) | 4 |
| PEG-2 oleate | Nikkol MYO-2 (Nikko) | 4.5 |
| PBG-4 laurate | Mapeg ® 200 ML (PPG), Kessco ® PEG 200 ML (Stepan), LIPOPEG 2L (LIPO Chem.) | 9.3 |
| PEG-4 oleate | Mapeg ® 200 MO (PPG), Kessco ® PEG 200 MO (Stepan), | 8.3 |
| PEG-4 stearate | Kessco ® PEG 200 MS (Stepan), Hodag 20 S (Calgenc), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), Kessco ® PEG 300 MO (Stepan), Nikkol MYO-6 (Nikko), Emulgante A6 (Condea) | 8.5 |
| PEG-7 oleate | Aigon OL 70 (Auschem SpA) | 10.4 |
| PEG-6 laurate | Kessco ® PEG 300 ML (Stepan) | 11.4 |
| PEG-7 laurate | Lauridac 7 (Condea) | 13 |
| PEG-6 stearate | Kessco ® PEG 300 MS (Stepan) | 9.7 |
| PEG-8 laurate | Mapeg ® 400 ML (PPG), LIPOPEG 4DL (Lipo Chem.) | 13 |
| PEG-8 oleate | Mapeg ® 400 MO (PPG), Emulgante A8 (Condea) | 12 |
| PEG-8 stearate | Mapeg ® 400 MS (PPG), Myrj 45 | 12 |
| PEG-9 oleate | Emulgante A9 (Condea) | >10 |
| PEG-9 stearate | Cremophor S9 (BASF) | >10 |
| PEG-10 laurate | Nikkol MYL-10 (Nikko), Lauridac 10 (Croda) | 13 |
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | Kessco ® PEG 600 ML (Stepan) | 15 |
| PEG-12 oleate | Kessco ® PEG 600 ML (Stepan) | 14 |
| PEG-12 ricinoleate | (CAS # 9004-97-1) | >10 |

TABLE 1-continued

PEG-Fatty Acid Monoester Surfactants

| COMPOUND | COMMERCIAL PRODUCT (Supplier) | HLB |
|---|---|---|
| PEG-12 stearate | Mapeg ® 600 MS (PPG), Kessco ® PEG 600 MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | Kessco ® PEG 1000 ML (Stepan) | 17 |
| PEG-20 oleate | Kessco ® PEG 1000 MO (Stepan) | 15 |
| PEG-20 stearate | Mapeg ® 1000 MS (PPG), Kessco ® PEG 1000 MS (Stepan), Myrj 49 | 16 |
| PEG-25 stearate | Nikkol MYS-25 (Nikko) | 15 |
| PEG-32 laurate | Kessco ° PEG 1540 ML (Stepan) | 16 |
| PEG-32 oleate | Kessco ® PEG 1540 MO (Stepan) | 17 |
| PEG-32 stearate | Kessco ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet O-100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf.) | >10 |

3.2 PEG-Fatty Acid Diesters

Polyethylene glycol fatty acid diesters are also suitable for use as surfactants in the compositions of the present invention. Representative PEG-fatty acid diesters are shown in Table 2. Among the surfactants in Table 2, preferred hydrophilic surfactants include PEG-20 dilaurate, PEG-20 dioleate, PEG-20 distearate, PEG-32 dilaurate and PEG-32 dioleate.

TABLE 2

PEG-Fatty Acid Diester Surfactants

| COMPOUND | COMMERCIAL PRODUCT (Supplier) | HLB |
|---|---|---|
| PEG-4 dilaurate | Mapeg ® 200 DL (PPG), Kessco ® PEG 200 DL (Stepan), LIPOPEG 2-DL (Lipo Chem.) | 7 |
| PEG-4 dioleate | Mapeg ® 200 DO (PPG), | 6 |
| PEG-4 distearate | Kessco ® 200 DS (Stepan_ | 5 |
| PEG-6 dilaurate | Kessco ® PEG 300 DL (Stepan) | 9.8 |
| PEG-6 dioleate | Kessco ® PEG 300 DO (Stepan) | 7.2 |
| PEG-6 distearate | Kessco ® PEG 300 DS (Stepan) | 6.5 |
| PEG-8 dilaurate | Mapeg ® 400 DL (PPG), Kessco ® PEG 400 DL (Stepan), LIPOPEG 4 DL (Lipo Chem.) | 11 |
| PEG-8 dioleate | Mapeg ® 400 DO (PPG), Kessco ® PEG 400 DO (Stepan), LIPOPEG 4 DO (Lipo Chem.) | 8.8 |
| PEG-8 distearate | Mapeg ® 400 DS (PPG), CDS 400 (Nikkol) | 11 |
| PEG-10 dipalmitate | Polyaldo 2PKFG | >10 |
| PEG-12 dilaurate | Kessco ® PEG 600 DL (Stepan) | 11.7 |
| PEG-12 distearate | Kessco ® PEG 600 DS (Stepan) | 10.7 |
| PEG-12 dioleate | Mapeg ® 600 DO (PPG), Kessco ® 600 DO (Stepan) | 10 |
| PEG-20 dilaurate | Kessco ® PEG 1000 DL (Stepan) | 15 |
| PEG-20 dioleate | Kessco ® PEG 1000 DO (Stepan) | 13 |
| PEG-20 distearate | Kessco ® PEG 1000 DS (Stepan) | 12 |
| PEG-32 dilaurate | Kessco ® PEG 1540 DL (Stepan) | 16 |
| PEG-32 dioleate | Kessco ® PEG 1540 DO (Stepan) | 15 |

TABLE 2-continued

PEG-Fatty Acid Diester Surfactants

| COMPOUND | COMMERCIAL PRODUCT (Supplier) | HLB |
|---|---|---|
| PEG-32 distearate | Kessco ® PEG 1540 DS (Stepan) | 15 |
| PEG-400 dioleate | Cithrol 4DO series (Croda) | >10 |
| PEG-400 distearate | Cithrol 4DS series (Croda) | >10 |

3.3 PEG-Fatty Acid Mono- and Di-ester Mixtures

In general, mixtures of surfactants are also useful in the present invention, including mixtures of two or more commercial surfactant products. Several PEG-fatty acid esters are marketed commercially as mixtures or mono- and diesters. Representative surfactant mixtures are shown in Table 3.

TABLE 3

PEG-Fatty Acid Mono- and Diester Mixtures

| COMPOUND | COMMERCIAL PRODUCT (Supplier) | HLB |
|---|---|---|
| PEG 4–150 mono, dilaurate | Kessco ® PEG 200–6000 mono, dilaurate (Stepan) | |
| PEG 4–150 mono, dioleate | Kessco ® PEG 200–6000 mono, dioleate (Stepan) | |
| PEG 4–150 mono, distearate | Kessco ® 200–6000 mono, distearate (Stepan) | |

3.4 Polyethylene Glycol Glycerol Fatty Acid Esters

Suitable PEG glycerol fatty acid esters are shown in Table 4. Among the surfactants in the Table, preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

TABLE 4

PEG Glycerol Fatty Acid Esters

| COMPOUND | COMMERCIAL PRODUCT (Supplier) | HLB |
|---|---|---|
| PEG-20 glyceryl laurate | Tagat ® L (Goldschmidt) | 16 |
| PEG-30 glyceryl laurate | Tagatr L2 (Goldschmidt) | 16 |
| PEG-15 glyceryl laurate | Glycerox L series (Croda) | 15 |
| PEG-40 glyceryl laurate | Glycerox L series (Croda) | 15 |
| PEG-20 glyceryl stearate | Capmul ® EMG (ABITEC), Aldo ® MS-20 KFG (Lonza) | 13 |
| PEG-20 glyceryl oleate | Tagat ® O (Goldschmidt) | >10 |
| PEG-30 glyceryl oleate | Tagat ® O2 (Goldschmidt) | >10 |

3.5. Alcohol-Oil Transesterification Products

A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil M 2735 CS), PEG-8 corn oil (Labrafil® WI, 2609 BS), PEG-20 corn glycerides (Crovol M40), and PEG-20 almond glycerides (Crovol A40). The latter two surfactants are reported to have HLB values of 10, which is generally considered to be the approximate border line between hydrophilic and hydrophobic surfactants. For purposes of the present invention, these two surfactants are considered to be hydrophobic. Representative surfactants of this class suitable for use in the present invention are shown in Table 5.

TABLE 5

Transesterification Products of Oils and Alcohols

| COMPOUND | COMMERCIAL PRODUCT (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6–7 |
| PEG-20 castor oil | Emalex C-20 (Nihon Emulsion), Nikkol CO-20 TX (Nikko) | 11 |
| PEG-23 castor oil | Emutgante EL23 | >10 |
| PEG-30 castor oil | Emalex C-30 (Nihon Emulsion), Alkamuls ® EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), Alkamuls ® EL 719 (Rhone-Poulenc) | 13 |
| PEG-50 castor oil | Emalex C-50 (Nihon Emulsion) | 14 |
| PEG-56 castor oil | Eumulgin ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin ® PRT 200 (Pulcra SA) | >10 |
| PEG-5 hydrogenated castor oil | Nikkol HCO-5 (Nikko) | 6 |
| PEG-7 hydrogenated caster oil | Simusol ® 989 (Seppic), Cremophor WO7 (BASF) | 6 |
| PEG-10 hydrogenated castor oil | Nikkol RCO-10 (Nikko) | 6.5 |
| PEG-20 hydrogenated castor oil | Nikkol HCO-20 (Nikko) | 11 |
| PEG-25 hydrogenated castor oil | Simulsol ® 1292 (Seppic), Cerex ELS 250 (Auschem SpA) | 11 |
| PEG-30 hydrogenated castor oil | Nikkol HCO-30 (Nikko) | II |
| PEG-40 hydrogenated castor oil | Cremophor RH 40 (BASF), (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO-60 (Nikko); Cremophor RH 60 (BASF) | 15 |

TABLE 5-continued

Transesterification Products of Oils and Alcohols

| COMPOUND | COMMERCIAL PRODUCT (Supplier) | HLB |
|---|---|---|
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil ® M 2125 CS (Gattefosse) | 4 |
| PEG-6 almond oil | Labrafil ® M 1966 CS (Gattefosse) | 4 |
| PEG-6 apricot kernel oil | Labrafil ® M 1944 CS (Gattefosse) | 4 |
| PEG-6 olive oil | Labrafil ® M 1980 CS (Gattefosse) | 4 |
| PEG-6 peanut oil | Labrafil ® M 1969 CS (Gattefosse) | 4 |
| PEG-6 hydrogenated palm kernel oil | Labrafil ® M 2130 BS (Gattefosse) | 4 |
| PEG-6 palm kernel oil | Labrafil ® M 2130 CS (Gattefosse) | 4 |
| PEG-6 triolein | Labrafil ® M 2735 CS (Gattefosse) | 4 |
| PEG-8 corn oil | Labrafil ® WL 2609 BS (Gattefosse) | 6–7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |
| PEG-60 corn glycerides | Crovol M70 (Croda) | 15 |
| PEG-60 almond glycerides | Crovol A70 (Croda) | 15 |
| PEG-4 caprylic/capric triglyceride | Labrafac ® Hydro (Gattefosse), | 4–5 |
| PEG-8 caprylic/capric glycerides | Labrasol (Gattefosse), Labrafac CM 10 (Gattefosse) | >10 |
| PEG-6 caprylic/capric glycerides | SOFTIGEN ® 767 (Hüls), Glycerox 767 (Croda) | 19 |
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetra esters of vegetable oils and sorbitol | SorbitoGlyceride (Gattefosse) | <10 |
| Pentaerythrityl tetraisostearate | Crodamol PTIS (Croda) | <10 |
| Pentaerythrityl distearate | Albunol DS (Taiwan Surf.) | <10 |
| Pentaerythrityl tetraoleate | Liponate PO-4 (Lipo Chem.) | <10 |
| Pentaerythrityl tetrastearate | Liponate PS-4 (Lipo Chem.) | <10 |
| Pentaerythrityl tetracaprylate/tetracaprate | Liponate PE-810 (Lipo Chem.), Crodamol PTC (Croda) | <10 |
| Pentaerythrityl tetraoctanoate | Nikkol Pentarate 408 (Nikko) | |

Also included as oils in this category of surfactants are oil-soluble vitamins, such as vitamins A, D, E, K, etc. Thus, derivatives of these vitamins, such as tocopheryl PEG-1000 succinate (TPGS, available from Eastman), are also suitable surfactants.

3.6. Polyglycerized Fatty Acids

Polyglycerol esters of fatty acids are also suitable surfactants for the present invention. Among the polyglyceryl fatty acid esters, preferred hydrophobic surfactants include polyglyceryl oleate (Plurol Oleique), polyglyceryl-2 dioleate (Nikkol DGDO), and polyglyceryl-10 trioleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860). Polyglyceryl polyricinoleates (Polymuls) are also preferred hydrophilic and hydrophobic surfactants. Examples of suitable polyglyceryl esters are shown in Table 6.

TABLE 6

Polyglycerized Fatty Acids

| COMPOUND | COMMERCIAL PRODUCT (Supplier) | HLB |
|---|---|---|
| Polyglyceryl-2 stearate | Nikkol DGMS (Nikko) | 5–7 |
| Polyglyceryl-2 oleate | Nikkol DGMO (Nikko) | 5–7 |
| Polyglyceryl-2 isostearate | Nikkol DGMIS (Nikko) | 5–7 |
| Polyglyceryl-3 oleate | Caprol ® 3GO (ABITEC), Drewpol 3-I-O (Stepan) | 6.5 |
| Polyglyceryl-4 oleate | Nikkol Tetraglyn 1-O (Nikko) | 5–7 |
| Polyglyceryl-4 stearate | Nikkol Tetraglyn 1 -S (Nikko) | 5–6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | >8 |
| Polyglyceryl-10 linoleate | Nikkol Decaglyn 1-LN (Nikko) | 12 |
| Polyglyceryl-6 pentaoleate | Nikkol Hexaglyn 5-O (Nikko) | <10 |
| Polyglyceryl-3 dioleate | Cremophor GO32 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |
| Polyglyceryl-6 dioleate | Caprol ® 6G20 (ABITEC); Hodag PGO-62 (Calgene), PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyeryl-10 pentaoleate | Nikkol Decaglyn 5-O (Nikko) | 3.5 |
| Polyglyceryl-10 septaoleate | Nikkol Decaglyn 7-O (Nikko) | 3 |
| Polyglyceryl-10 tetraoleate | Caprol ® 10G40 (ABITEC); Hodag PGO-62 (CALGENE), Drewpol 104-O (Stepan) | 6.2 |
| Polyglyceryl-10 decaisostearate | Nikkol Decaglyn 10-IS (Nikko) | <10 |
| Polyglyceryl-10l decoaleate | Drewpol 10-10-O (Stepan), Caprol 10G10O (ABITEC), Nikkol Decaglyn 10-O | 3.5 |
| Polyglyceryl-10 mono, dioleate | Caprol ® PGE 860 (ABITEC) | 11 |
| Polyglyceryl polyricinoleate | Polymuls (Henkel) | 3–20 |

3.7. Propylene Glycol Fatty Acid Esters

Esters of propylene glycol and fatty acids are suitable surfactants for use in the present invention. In this surfactant class, preferred hydrophobic surfactants include propylene glycol monolaurate (Lauroglycol FCC), propylene glycol ricinoleate (Propymuls), propylene glycol monooleate (Myverol P-O6), propylene glycol dicaprylate/dicaprate (Captex® 200), and propylene glycol dioctanoate (Captex® 800). Examples of surfactants of this class are given in Table 7.

TABLE 7

Propylene Glycol Fatty Acid Esters

| COMPOUND | COMMERCIAL PRODUCT (Supplier) | HLB |
|---|---|---|
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo ® PGHMS (Lonza) | 3–4 |
| Propylene glycol hydroxy stearate | | <10 |
| Propylene glycol ricinoleate | PROPYMULS (Henkel) | <10 |
| Propylene glycol isostearate | | <10 |
| Propylene glycol monooleate | Myverol P-06 (Eastman) | <10 |
| Propylene glycol dicaprylate/dicaprate | Captex ® 200 (ABITEC), Miglyol ® 840 (Hüls), Neobee ® M-20 (Stepan) | >6 |
| Propylene glycol dioctanoate | Captex ® 800 (ABITEC) | >6 |
| Propylene glycol caprylate/caprate | LABRAFAC PG (Gattefosse) | >6 |
| Propylene glycol dilaurate | | >6 |
| Propylene glycol distearate | Kessco ® PGDS (Stepan) | >6 |
| Propylene glycol dicaprylate | Nikkol Sefsol 228 (Nikko) | >6 |
| Propylene glycol dicaprate | Nikkol PDD (Nikko) | >6 |

3.8. Mixtures of Propylene Glycol Esters—Glycerol Esters

In general, mixtures of surfactants are also suitable for use in the present invention. In particular, mixtures of propylene glycol fatty acid esters and glycerol fatty acid esters are suitable and are commercially available. One preferred mixture is composed of the oleic acid esters of propylene glycol and glycerol (Arlacel 186). Examples of these surfactants are shown in Table 8.

TABLE 8

Glycerol/Propylene Glycol Fatty Acid Esters

| COMPOUND | COMMERCIAL PRODUCT (Supplier) | HLB |
|---|---|---|
| Oleic | ATMOS 300, ARLACEL 186 (ICI) | 3–4 |
| Stearic | ATMOS 150 | 3–4 |

3.9. Mono- and Diglycerides

A particularly important class of surfactants is the class of mono- and diglycerides. These surfactants are generally hydrophobic. Preferred hydrophobic surfactants in this class of compounds include glyceryl monooleate (Peceol), glyceryl ricinoleate, glyceryl laurate, glyceryl dilaurate (Capmul® GDL), glyceryl dioleate (Capmul® GDO), glyceryl mono/dioleate (Capmul® GMO-K), glyceryl caprylate/caprate (Capmul(® MCM), caprylic acid mono/diglycerides (Imwitor® 988), and mono- and diacetylated monoglycerides (Myvacet® 9-45). Examples of these surfactants are given in Table 9.

TABLE 9

Mono- and Diglyceride Surfactants

| COMPOUND | COMMERCIAL PRODUCT (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3–4 |
| Glyceryl monooleate (C18:1) | PECEOL (Gattefosse), Hodag GMO-D, Nikkol MGO (Nikko) | 3–4 |
| Glyceryl monooleate | RYLO series (Danisco), DIMODAN series (Danisco), EMULDAN (Danisco), ALDO ® MO FG (Lonza), Kessco GMO (Stepan), MONOMULS ® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | 3–4 |
| Glycerol monooleate/linoleate | OLICINE (Gattefosse) | 3–4 |
| Glycerol monolinoleate | Maisine (Gattefosse), MYVEROL 18-92, Myverol 18-06 (Eastman) | 3–4 |
| Glyceryl ricinoleate | Softigen ® 701 (Hüls), HODAG GMR-D (Calgene), ALDO ® MR (Lonza) | 6 |
| Glyceryl monolaurate | ALDO ® MLD (Lonza), Hodag GML (Calgene) | 6.8 |
| Glycerol monopalmitate | Emalex GMS-P (Nihon) | 4 |
| Glycerol monostearate | Capmul ® GMS (ABITEC), Myvaplex (Eastman), IMWITOR ® 191 (Hüls), CUTINA GMS, Aldo ® MS (Lonza), Nikkol MGS series (Nikko) | 5–9 |
| Glyceryl mono-, dioleate | Capmul ® GMO-K (ABITEC) | <10 |
| Glyceryl palmitic/stearic | CUTINA MD-A, ESTAGEL-G18 | <10 |
| Glyceryl acetate | Lamegin ® EE (Grünau GmbH) | <10 |
| Glyceryl laurate | Imwitor ® 312 (Hüls), Monomuls ® 90-45 (Grünau GmbH), Aldo ® MLD (Lonza) | 4 |
| Glyceryl citrate/lactate/oleate/linoleate | Imwitor ® 375 (Hüls) | <10 |
| Glyceryl caprylate | Imwitor ® 308 (Hüls), Capmul ® MCMC8 (ABITEC) | 5–6 |
| Glyceryl caprylate/caprate | Capmul ® MCM (ABITEC) | 5–6 |
| Caprylic acid mono, diglycerides | Imwitor ® 988 (Hüls) | 5–6 |
| Caprylic/capric glycerides | Imwitor ® 742 (Hüls) | <10 |
| Mono-and diacetylated monoglycerides | Myvacet ® 9-45, Myvacet ® 9-40, Myvacet ® 9-08 (Eastman), Lamegin ® (Grünau) | 3.8–4 |
| Glyceryl monostearate | Aldo ® MS, Arlacel 129 (ICI), LIPO GMS (Lipo Chem.), Imwitor ® 191 (Hüls), Myvaplex (Eastman) | 4.4 |
| Lactic acid esters of mono,diglycerides | LAMEGIN GLP (Henkel) | |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | <10 |
| Distearin | (Larodan) | <10 |
| Glyceryl dilaurate (C12) | Capmul ® GDL (ABITEC) | 3–4 |
| Glyceryl dioleate | Capmul ® GDO (ABITEC) | 3–4 |
| Glycerol esters of fatty acids | GELUCIRE 39/01 (Gattefosse), GELUCIRE 43/01 (Gattefosse) | 1 |
| | GELUCIRE 37/06 (Gattefosse) | 6 |
| Dipalmitolein (C16:1) | (Larodan) | <10 |

TABLE 9-continued

Mono- and Diglyceride Surfactants

| COMPOUND | COMMERCIAL PRODUCT (Supplier) | HLB |
|---|---|---|
| 1,2 and 1,3-diolein (C18:1) | (Larodan) | <10 |
| Dielaidin (C18:1) | (Larodan) | <10 |
| Dilinolein (C18:2) | (Larodan) | <10 |

3.10. Sterol and Sterol Derivatives

Sterols and derivatives of sterols are suitable surfactants for use in the present invention. These surfactants can be hydrophilic or hydrophobic. Preferred derivatives include the polyethylene glycol derivatives. A preferred hydrophobic surfactant in this class is cholesterol. A preferred hydrophilic surfactant in this class is PEG-24 cholesterol ether (Solulan C-24). Examples of surfactants of this class are shown in Table 10.

TABLE 10

Sterol and Sterol Derivative Surfactants

| COMPOUND | COMMERCIAL PRODUCT (Supplier) | HLB |
|---|---|---|
| Cholesterol, sitosterol, lanosterol | | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-5 (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

3.11. Polyethylene Glycol Sorbitan Fatty Acid Esters

A variety of PEG-sorbitan fatty acid esters are available and are suitable for use as surfactants in the present invention. In general, these surfactants are hydrophilic, although several hydrophobic surfactants of this class can be used. Among the PEG-sorbitan fatty acid esters, preferred hydrophilic surfactants include PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80). Examples of these surfactants are shown in Table 11.

TABLE 11

PEG-Sorbitan Fatty Acid Esters

| COMPOUND | COMMERCIAL PRODUCT (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan monolaurate | Nikkol GL-1 (Nikko) | 16 |
| PEG-20 sorbitan monopalmitate | Tween-40 (Atlas/ICI), Crillet 2 (Croda) | 16 |
| PEG-20 sorbitan monostearate | Tween-60 (Atlas/ICI), Crillet 3 (Croda) | 15 |
| PEG-4 sorbitan monostearate | Tween-61 (Atlas/ICI), Crillet 31 (Croda) | 9.6 |
| PEG-8 sorbitan monostearate | DACOL MSS (Condea) | >10 |
| PEG-6 sorbitan monostearate | Nikkol TS106 (Nikko) | 11 |
| PEG-20 sorbitan tristearate | Tween-65 (Atlas/ICI), Crillet 35 (Croda) | 11 |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040 (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoleate | Nikkol GO-430 (Nikko) | 12 |
| PEG-40 sorbitan tetraoleate | Nikkol GO-440 (Nikko) | 13 |
| PEG-20 sorbitan monoisostearate | Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

3.12. Polyethylene Glycol Alkyl Ethers

Ethers of polyethylene glycol and alkyl alcohols are suitable surfactants for use in the present invention. Preferred hydrophobic ethers include PEG-3 oleyl ether (Volpo 3) and PEG-4 lauryl ether (Brij 30). Examples of these surfactants are shown in Table 12.

TABLE 12

Polyethylene Glycol Alkyl Ethers

| COMPOUND | COMMERCIAL PRODUCT (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

3.13. Sugar Esters

Esters of sugars are suitable surfactants for use in the present invention. Preferred hydrophilic surfactants in this class include sucrose monopalmate and sucrose monolaurate. Examples of such surfactants are shown in Table 13.

TABLE 13

Sugar Ester Surfactants

| COMPOUND | COMMERCIAL PRODUCT (Supplier) | HLB |
|---|---|---|
| Sucrose distearate | SUCRO ESTER 7 (Gattefosse), Crodesta F-10 (Croda) | 3 |
| Sucrose distearate/monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

3.14. Polyethylene Glycol Alkyl Phenols

Several hydrophilic PEG-alkyl phenol surfactants are available, and are suitable for use in the present invention. Examples of these surfactants are shown in Table 14.

TABLE 14

Polyethylene Glycol Alkyl Phenol Surfactants

| COMPOUND | COMMERCIAL PRODUCT (Supplier) | HLB |
|---|---|---|
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

3.15. Polyoxyethylene-Polyoxypropylene Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula:

$$HO(C_2H_4O)_a(C_3H_6O)_b(C_2H_4O)_aH$$

where "a" and "b" denote the number of polyoxyethylene and polyoxypropylene units, respectively.

Preferred hydrophilic surfactants of this class include poloxamers 108, 188, 217, 238, 288, 338, and 407. Preferred hydrophobic surfactants in this class include poloxamers 124, 182, 183, 212, 331, and 335.

Examples of suitable surfactants of this class are shown in Table 15. Since the compounds are widely available, commercial sources are not listed in the Table. The compounds are listed by generic name, with the corresponding "a" and "b" values.

TABLE 15

POE-POP Block Copolymers

| COMPOUND | a, b values in $HO(C_2H_4O)_a(C_3H_6O)_b(C_2H_4O)_aH$ | | HLB |
|---|---|---|---|
| Poloxamer 105 | a = 11 | b = 16 | 8 |
| Poloxamer 108 | a = 46 | b = 16 | >10 |

TABLE 15-continued

POE-POP Block Copolymers

| COMPOUND | a, b values in $HO(C_2H_4O)_a(C_3H_6O)_b(C_2H_4O)_aH$ | | HLB |
|---|---|---|---|
| Poloxamer 122 | a = 5 | b = 21 | 3 |
| Poloxamer 123 | a = 7 | b = 21 | 7 |
| Poloxamer 124 | a = 11 | b = 21 | >7 |
| Poloxamer 181 | a = 3 | b = 30 | |
| Poloxamer 182 | a = 8 | b = 30 | 2 |
| Poloxamer 183 | a = 10 | b = 30 | |
| Poloxamer 184 | a = 13 | b = 30 | |
| Poloxamer 185 | a = 19 | b = 30 | |
| Poloxamer 188 | a = 75 | b = 30 | 29 |
| Poloxamer 212 | a = 8 | b = 35 | |
| Poloxamer 215 | a = 24 | b = 35 | |
| Poloxamer 217 | a = 52 | b = 35 | |
| Poloxamer 231 | a = 16 | b = 39 | |
| Poloxamer 234 | a = 22 | b = 39 | |
| Poloxamer 235 | a = 27 | b = 39 | |
| Poloxamer 237 | a = 62 | b = 39 | 24 |
| Poloxamer 238 | a = 97 | b = 39 | |
| Poloxamer 282 | a = 10 | b = 47 | |
| Poloxamer 284 | a = 21 | b = 47 | |
| Poloxamer 288 | a = 122 | b = 47 | >10 |
| Poloxamer 331 | a = 7 | b = 54 | 0.5 |
| Poloxamer 333 | a = 20 | b = 54 | |
| Poloxamer 334 | a = 31 | b = 54 | |
| Poloxamer 335 | a = 38 | b = 54 | |
| Poloxamer 338 | a = 128 | b = 54 | |
| Poloxamer 401 | a = 6 | b = 67 | |
| Poloxamer 402 | a = 13 | b = 67 | |
| Poloxamer 403 | a = 21 | b = 67 | |
| Poloxamer 407 | a = 98 | b = 67 | |

3.16. Sorbitan Fatty Acid Esters

Sorbitan esters of fatty acids are suitable surfactants for use in the present invention. Among these esters, preferred hydrophobic surfactants include sorbitan monolaurate (Arlacel 20), sorbitan monopalmitate (Span-40), sorbitan monooleate (Span-80), sorbitan monostearate, and sorbitan tristearate. Examples of these surfactants are shown in Table 16.

TABLE 16

Sorbitan Fatty Acid Ester Surfactants

| COMPOUND | COMMERCIAL PRODUCT (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

3.17. Lower Alcohol Fatty Acid Esters

Esters of lower alcohols ($C_2$ to $C_4$) and fatty acids ($C_8$ to $C_{18}$) are suitable surfactants for use in the present invention. Among these esters, preferred hydrophobic surfactants include ethyl oleate (Crodamol EO), isopropyl myristate (Crodamol IPM), and isopropyl palmitate (Crodamol IPP). Examples of these surfactants are shown in Table 17.

TABLE 17

Lower Alcohol Fatty Acid Ester Surfactants

| COMPOUND | COMMERCIAL PRODUCT (Supplier) | HLB |
|---|---|---|
| Ethyl oleate | Crodamol EO (Croda); Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

3.18. Ionic Surfactants

Ionic surfactants, including cationic, anionic and zwitterionic surfactants, are suitable hydrophilic surfactants for use in the present invention. Preferred anionic surfactants include fatty acid salts and bile salts. Specifically, preferred ionic surfactants include sodium oleate, sodium lauryl sulfate, sodium lauryl sarcosinate, sodium dioctyl sulfosuccinate, sodium cholate, and sodium taurocholate. Examples of such surfactants are shown in Table 18. For simplicity, typical counterions are shown in the entries in the Table. It will be appreciated by one skilled in the art, however, that any bioacceptable counterion may be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

TABLE 18

Ionic Surfactants

| COMPOUND | HLB |
|---|---|
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glyco cheno deoxycholate | |
| Sodium cholylsarcosinate | |
| Sodium N-methyl taurocholate | |

TABLE 18-continued

Ionic Surfactants

| COMPOUND | HLB |
|---|---|
| PHOSPHOLIPIDS | |
| Egg/Soy lecithin [Epikuron ™ (Lucas Meyer), Ovothin ™ (Lucas Meyer)] | |
| Lyso egg/soy lecithin | |
| Hydroxylated lecithin | |
| Lysophosphatidylcholine | |
| Cardiolipin | |
| Sphingomyelin | |
| Phosphatidylcholine | |
| Phosphatidyl ethanolamine | |
| Phosphatidic acid | |
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates: | |
| lactylic esters of fatty acids | |
| calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Hexadecyl triammonium bromide | |
| Decyl trimethyl ammonium bromide | |
| Cetyl trimethyl ammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
| Lauryl betaine (N-lauryl,N,N-dimethylglycine) | |
| Ethoxylated amines: | |
| Polyoxyethylene-15 coconut amine | |

It is surprisingly found that pharmaceutical compositions of ionizable hydrophobic therapeutic agents including at least one surfactant in the carrier are capable of delivering the therapeutic agent without suffering from precipitation of the therapeutic agent in the gastrointestinal tract. In conventional formulations containing an ionizable hydrophobic therapeutic agent and an ionizing agent, the ionizing agent ionizes the therapeutic agent, enabling it to be solubilized. Upon dilution by ambient fluids in the gastrointestinal tract, and exposure to the pH conditions therein, however, such conventional formulations are prone to precipitation of the therapeutic agent. Thus, while the addition of an ionizing agent provides a dosage form of solubilized therapeutic agent, solubilization in vivo remains problematic. In contrast, the formulations of the present invention maintain the therapeutic agent in solubilized form by protecting the therapeutic agent with a surfactant.

Preferably, the carrier includes at least one non-ionic surfactant selected from the group consisting of alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; sugar esters, sugar ethers; sucroglycerides; and mixtures thereof.

More preferably, the non-ionic hydrophilic surfactant is selected from the group consisting of polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; and polyoxyethylene hydrogenated vegetable oils. The glyceride can be a monoglyceride, diglyceride, triglyceride, or a mixture.

Also preferred are non-ionic hydrophilic surfactants that a-re reaction mixtures of polyols and fatty acids, glycerides, vegetable oils, hydrogenated vegetable oils or sterols. These reaction mixtures are largely composed of the transesterification products of the reaction, along with often complex mixtures of other reaction products. The polyol is preferably glycerol, ethylene glycol, polyethylene glycol, sorbitol, propylene glycol, or pentaerythritol.

Several particularly preferred carrier compositions are those which include as a non-ionic hydrophilic surfactant PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, or a poloxamer.

Among these preferred surfactants, more preferred are PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-10 laurate, PEG-6 caprate/caprylate glycerides, PEG-8 caprate/caprylate glycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate and poloxamers. Most preferred are PEG-35 castor oil, PEG-40 hydrogenated castor oil, PEG-60 corn oil, PEG-25 glyceryl trioleate, PEG-6 caprate/caprylate glycerides, PEG-8 caprate/caprylate glycerides, polysorbate 20, polysorbate 80, tocopheryl PEG-1000 succinate, PEG-24 cholesterol, and hydrophilic poloxamers.

In carrier compositions that include at least one hydrophobic surfactant, the hydrophobic surfactant is preferably a surfactant selected from the group consisting of alcohols; polyoxyethylene alkylethers; fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; and polyoxyethylene hydrogenated vegetable oils.

As with the hydrophilic surfactants, hydrophobic surfactants can be reaction mixtures of polyols and fatty acids, glycerides, vegetable oils, hydrogenated vegetable oils, and sterols.

Preferably, the hydrophobic surfactant is selected from the group consisting of fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, and sterols.

More preferred are lower alcohol fatty acids esters; polypropylene glycol fatty acid esters; propylene glycol fatty acid esters; glycerol fatty acid esters; acetylated glycerol fatty acid esters; lactic acid derivatives of mono/diglycerides; sorbitan fatty acid esters; polyoxyethylene vegetable oils; and mixtures thereof, with glycerol fatty acid esters and acetylated glycerol fatty acid esters being most preferred. Among the glycerol fatty acid esters, the esters are preferably mono- or diglycerides, or mixtures of mono- and diglycerides, where the fatty acid moiety is a $C_6$ to $C_{20}$ fatty acid. Also preferred are hydrophobic surfactants which are the reaction mixture of polyols and fatty acids, glycerides, vegetable oils, hydrogenated vegetable oils, and sterols. Preferred polyols are polyethylene glycol, sorbitol, propylene glycol, and pentaerythritol. Specifically preferred hydrophobic surfactants include myristic acid; oleic acid; lauric acid; stearic acid; palmitic acid; PEG 1-4 stearate; PEG 2-4 oleate; PEG-4 dilaurate; PEG-4 dioleate; PEG-4 distearate; PEG-6 dioleate; PEG-6 distearate; PEG-8 dioleate; PEG 3-16 castor oil; PEG 5-10 hydrogenated castor oil; PEG 6-20 corn oil; PEG 6-20 almond PEG-6 olive oil; PEG-6 peanut oil; PEG-6 palm kernel oil; PEG-6 hydrogenated palm kernel oil; PEG-4 capric/caprylic triglyceride, mono, di, tri, tetra esters of vegetable oil and sorbitol; pentaerythrityl di, tetra stearate, isostearate, oleate. caprylate, or caprate; polyglyceryl 2-4 oleate, stearate, or isostearate; polyglyceryl 4-10 pentaoleate; polyglyceryl-3 dioleate; polyglyceryl-6 dioleate; polyglyceryl-10 trioleate; polyglyceryl-3 distearate; propylene glycol mono- or diesters of a $C_6$ to $C_{20}$ fatty acid; monoglycerides of $C_6$ to $C_{20}$ fatty acids; acetylated monoglycerides of $C_6$ to $C_{20}$ fatty acids; diglycerides of $C_6$ to $C_{20}$ fatty acids; lactic acid derivatives of monoglycerides; lactic acid derivatives of diglycerides; cholesterol; phytosterol; PEG 5-20 soya sterol; PEG-6 sorbitan tetra, hexastearate; PEG-6 sorbitan tetraoleate; sorbitan monolaurate sorbitan monopalmitate; sorbitan mono, trioleate; sorbitan mono, tristearate; sorbitan monoisostearate; sorbitan sesquioleate; sorbitan sesquistearate; PEG 2-5 oleyl ether; POE 2-4 lauryl ether; PEG-2 cetyl ether; PEG-2 stearyl ether; sucrose distearate; sucrose dipalmitate; ethyl oleate; isopropyl myristate; isopropyl palmitate; ethyl linoleate; isopropyl linoleate; and poloxamers.

Among the specifically preferred hydrophobic surfactants, most preferred are oleic acid; lauric acid; glyceryl monocaprate; glyceryl monocaprylate; glyceryl monolaurate; glyceryl monooleate; glyceryl dicaprate; glyceryl dicaprylate; glyceryl dilaurate; glyceryl dioleate; acetylated monoglycerides; propylene glycol oleate; propylene glycol laurate; polyglyceryl-3 oleate; polyglyceryl-6 dioleate; PEG-6 corn oil; PEG-20 corn oil; PEG-20 almond oil; sorbitan monooleate; sorbitan monolaurate; POE-4 lauryl ether; POE-3 oleyl ether; ethyl oleate; and poloxamers.

Also preferred are mixtures of at least one hydrophilic surfactant and at least one hydrophobic surfactant.

The surfactant or surfactant mixture is present in an amount sufficient to promote the continued solubilization of the therapeutic agent in the gastrointestinal tract. Although small amounts of surfactant may provide some stabilization of the solubilized therapeutic agent, it is presently preferred to include a surfactant in an amount of at least about 10%, preferably about 20-90% by weight, based on the total weight of the composition. Also preferred are mixtures of surfactants, wherein the total amount of surfactant is at least about 10%, and preferably about 20-90% by weight, based on the total weight of the composition.

4. Solubilizers

The carrier optionally includes one or more pharmaceutically acceptable solubilizers to enhance the solubility of the ionizable hydrophobic therapeutic agent in the carrier system. Examples of such compounds include:

alcohols and polyols, such as ethanol, isopropanol, butanol, benzyl alcohol, ethylene glycol, propylene glycol, butanediols and isomers thereof, glycerol, pentaerythritol, sorbitol, mannitol, dimethyl isosorbide, polyethylene glycol, polypropylene glycol, polyvinylalcohol, hydroxypropyl methylcellulose and other cellulose derivatives, maltodextrins, cyclodextrins and derivatives thereof;

ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide);

amides, such as 2-pyrrolidone, 2-piperidone, F-caprolactam, N-alkylpyrrolidone, N-hydroxyalkylpyrrolidone, N-alkylpiperidone, N-alkylcaprolactam, dimethylacetamide, and polyvinylpyrrolidone;

esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof;

and other solubilizers known in the art, such as dimethyl acetamide, dimethyl isosorbide (Arlasolve DMI (ICI)), N-methyl pyrrolidones (Pharmasolve (ISP)), transcutol, monooctanoin, and water.

Mixtures of solubilizers are also within the scope of the invention. Except as indicated, these compounds are readily available from standard commercial sources.

Preferred solubilizers include ethanol, isopropanol, butanol, benzyl alcohol, ethylene glycol, propylene glycol, butanediol and isomers thereof, glycerol, pentaerythritol, sorbitol, mannitol, dimethyl isosorbide, polyethylene glycol, polypropylene glycol, polyvinylalcohol, hydroxypropyl methylcellulose and other cellulose derivatives, maltodextrins, cyclodextrins and derivatives thereof, ethyl propionate, tributylcitrate, acetyl triethylcitrate, acetyl tributyl citrate, triethylcitrate, ethyl oleate, ethyl caprylate, ethyl butyrate, triacetin, propylene glycol diacetate, ε-caprolactone and isomers thereof, δ-valerolactone and isomers thereof, β-butyrolactone and isomers thereof, 2-pyrrolidone, 2-piperidone, ε-caprolactam, N-methylpyrrolidone, N-ethylpyrrolidone, N-hydroxyethyl pyrrolidone, N-octylpyrrolidone, N-laurylpyrrolidone, dimethylacetamide, polyvinylpyrrolidone, glycofurol, methoxy PEG, and mixtures thereof.

More preferred solubilizers are ethanol, isopropanol, benzyl alcohol, ethylene glycol, propylene glycol, 1,3-butanediol, glycerol, pentaerythritol, sorbitol, glycofurol, dimethyl isosorbide, polyethylene glycol, polyvinylalcohol, hydroxypropyl methylcellulose, methylcellulose, ethylcellulose, hydroxypropylcyclodextrins, sulfobutyl ether derivatives of cyclodextrins, ethyl propionate, tributylcitrate, triethylcitrate, ethyl oleate, ethyl caprylate, triacetin, β-butyrolactone and isomers thereof, 2-pyrrolidone, N-methylpyrrolidone, N-ethylpyrrolidone, N-hydroxyethylpyrrolidone, N-octylpyrrolidone, N-laurylpyrrolidone, dimethylacetamide, polyvinylpyrrolidone, and mixtures thereof.

Still more preferred are triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-600, glycofurol, propylene glycol, and dimethyl isosorbide. Most preferred solubilizers include sorbitol, glycerol, triacetin, ethyl alcohol, PEG-400, glycofurol and propylene glycol.

The amount of solubilizer that can be included in compositions of the present invention is not particularly limited. Of course, when such compositions are ultimately administered to a patient, the amount of a given solubilizer is limited to a bioacceptable amount. In some circumstances, it may be advantageous to include amounts of solubilizers far in excess of bioacceptable amounts in order to maximize the concentration of ionizable hydrophobic therapeutic agent, with excess solubilizer removed prior to providing the composition to a patient using conventional techniques, such as distillation or evaporation.

In a particular embodiment, the solubilizer includes at least one compound selected from the group consisting of alcohols, polyols, amides, esters, and propylene glycol ethers, the alcohol or polyol being selected from the group consisting of ethanol, isopropanol, butanol, benzyl alcohol, ethylene glycol, propylene glycol, butanediols and isomers thereof, glycerol, pentaerythritol, sorbitol, mannitol, dimethyl isosorbide, polypropylene glycol, polyvinylalcohol, hydroxypropyl methylcellulose and other cellulose derivatives, maltodextrins, and cyclodextrins and cyclodextrin derivatives. In this embodiment, the surfactant includes at least one compound selected from the group consisting of alkylglucosides; alkylmaltosides; alkylthioglucosides; lauryl macrogolglycerides; polyoxyethylene alkyl ethers; fatty acids; lower alcohol fatty acid esters; polyoxyethylene alkylphenols; polyethylene glycol fatty acids esters; polypropylene glycol fatty acid esters; glycerol fatty acid esters; acetylated glycerol fatty acid esters; polyethylene glycol glycerol fatty acid esters; polyglyceryl fatty acid esters; polyoxyethylene sorbitan fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, vegetable oils, hydrogenated vegetable oils, and sterols; sugar esters; sugar ethers; sucroglycerides; fatty acid salts; bile salts; phospholipids; phosphoric acid esters; carboxylates; sulfates; and sulfonates.

In another particular embodiment, the solubilizer is present in an amount of greater than about 10% by weight, based on the total weight of the composition. In this embodiment, the surfactant includes at least one compound from the group consisting of alkylglucosides; alkylmaltosides; alkylthioglucosides; lauryl macrogolglycerides; fatty acids; lower alcohol fatty acid esters; polyoxyethylene alkylphenols; polyethylene glycol fatty acid esters; polypropylene glycol fatty acid esters; glycerol fatty acid esters; acetylated glycerol fatty acid esters; polyethylene glycol glycerol fatty acid esters; polyglyceryl fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, vegetable oils, hydrogenated vegetable oils, and sterols; sugar esters, sugar ethers, sucroglycerides; fatty acid salts; bile salts; phospholipids; phosphoric acid esters; carboxylates; sulfates; and sulfonates.

5. Trizlycerides

The carrier may also include one or more pharmaceutically acceptable triglycerides to enhance the solubility of the ionizable hydrophobic therapeutic agent in the carrier system. Examples of triglycerides suitable for use in the present invention are shown in Table 19.

TABLE 19

| Triglycerides | |
|---|---|
| Triglyceride | Commercial Source |
| Almond oil | Super Refined Almond Oil (Croda) |
| Canola oil | Lipex 108 (Abitec) |
| Castor oil | |
| Coconut oil | Pureco 76 (Abitec) |
| Corn oil | Super Refined Corn Oil (Croda) |
| Cottonseed oil | Super Refined Cottonseed Oil (Croda) |
| Menhaden oil | Super Refined Menhaden Oil (Croda) |
| Olive oil | Super Refined Olive Oil (Croda) |
| Peanut oil | Super Refined Peanut Oil (Croda) |
| Safflower oil | Super Refined Safflower Oil (Croda) |
| Sesame oil | Super Refined Sesame Oil (Croda) |

TABLE 19-continued

| Triglycerides | |
|---|---|
| Triglyceride | Commercial Source |
| Shark liver oil | Super Refined Shark Liver Oil (Croda) |
| Soybean oil | Super Refined Soybean Oil (Croda) |
| Wheat germ oil | Super Refined Wheat Germ Oil (Croda) |
| Hydrogenated castor oil | Castorwax |
| Hydrogenated cottonseed oil | Dritex C (Abitec) |
| Hydrogenated palm oil | Dritex PST (Abitec); Softisan 154 (Hüls) |
| Hydrogenated soybean oil | Sterotex HM NF (Abitec); Dritex S (Abitec) |
| Hydrogenated vegetable oil | Sterotex NF (Abitec); Hydrokote M (Abitec) |
| Hydrogenated cottonseed and castor oil | Sterotex K (Abitec) |
| Partially hydrogenated soybean oil | Hydrokote AP5 (Abitec) |
| Partially soy and cottonseed oil | Apex B (Abitec) |
| Glyceryl tributyrate | (Sigma) |
| Glyceryl tricaproate | (Sigma) |
| Glyceryl tricaprylate | (Sigma) |
| Glyceryl tricaprate | Captex 1000 (Abitec) |
| Glyceryl triundecanoate | Captex 8227 (Abitec) |
| Glyceryl trilaurate | (Sigma) |
| Glyceryl trimyristate | Dynasan 114 (Hüls) |
| Glyceryl tripalmitate | Dynasan 116 (Hüls) |
| Glyceryl tristearate | Dynasan 118 (Hüls) |
| Glyceryl triarchidate | (Sigma) |
| Glyceryl trimyristoleate | (Sigma) |
| Glyceryl tripalmitoleate | (Sigma) |
| Glyceryl trioleate | (Sigma) |
| Glyceryl trilinoleate | (Sigma) |
| Glyceryl trilinolenate | (Sigma) |
| Glyceryl tricaprylate/caprate | Captex 300 (Abitec); Captex 355 (Abitec); Miglyol 810 (Hüls); Miglyol 812 (Hüls) |
| Glyceryl tricaprylate/caprate/laurate | Captex 350 (Abitec) |
| Glyceryl tricaprylate/caprate/linoleate | Captex 810 (Abitec); Miglyol 818 (Hüls) |
| Glyceryl tricaprylate/caprate/stearate | Softisan 378 (Hüls); (Larodan) |
| Glyceryl tricaprylate/laurate/stearate | (Larodan) |
| Glyceryl 1,2-caprylate-3-linoleate | (Larodan) |
| Glyceryl 1,2-caprate-3-stearate | (Larodan) |
| Glyceryl 1,2-laurate-3-myristate | (Larodan) |
| Glyceryl 1,2-myristate-3-laurate | (Larodan) |
| Glyceryl 1,3-palmitate-2-butyrate | (Larodan) |
| Glyceryl 1,3-stearate-2-caprate | (Larodan) |
| Glyceryl 1,2-linoleate-3-caprylate | (Larodan) |

Mixtures of triglycerides are also within the scope of the invention.

Preferred triglycerides include vegetable oils, fish oils, animal fats, hydrogenated vegetable oils, partially hydrogenated vegetable oils, medium and long-chain triglycerides, and structured triglycerides.

6. Other Additives

Other additives conventionally used in pharmaceutical compositions can be included, and these additives are well known in the art. Such additives include antioxidants, preservatives, chelating agents, complexing agents, viscomodulators, tonicifiers, flavorants, colorants odorants, opacifiers, suspending agents, binders, and mixtures thereof. The amounts of such additives can be readily determined by one skilled in the art, according to the particular properties desired.

7. Dosage Forms

The pharmaceutical compositions of the present invention can be provided in the form of a solution preconcentrate; i.e., a composition as described above, and intended to be dispersed with water, either prior to administration, in the form of a drink, or dispersed in vivo. Alternatively, the compositions can be provided in the form of a diluted preconcentrate (i.e., an aqueous dispersion), a semi-solid dispersion or a solid dispersion. If desired, the compositions may be encapsulated in a hard or soft gelatin capsule, a starch capsule or an enteric coated capsule. The term "enteric coated capsule" as used herein means a capsule coated with a coating resistant to acid; i.e., an acid resistant enteric coating.

Although formulations specifically suited to oral administration are presently preferred, the compositions of the present invention can also be formulated for topical, transdermal, ocular, pulmonary, vaginal, rectal, transmucosal or parenteral administration, in the form of a cream, lotion, ointment, suppository, gel or the like. If such a formulation is desired, other additives may be included, such as are well-known in the art, to impart the desired consistency and other properties to the formulation. The compositions of the present invention can also be formulated as a spray or an aerosol. In particular, the compositions may be formulated as a sprayable solution, and such formulation is particularly useful for spraying to coat a multiparticulate carrier, such as a bead. Such multiparticulate carriers are well known in the art.

8. Preparation of Pharmaceutical Compositions

The pharmaceutical compositions of the present invention can be prepared by conventional methods well known to those skilled in the art. Of course, the specific method of preparation will depend upon the ultimate dosage form. For dosage forms substantially free of water, i.e., when the composition is provided in a pre-concentrated form for later dispersion in an aqueous system, the composition is prepared by simple mixing of the components to form a pre-concentrate. The mixing process can be aided by gentle heating, if desired. For compositions in the form of an aqueous dispersion, the pre-concentrate form is prepared, then the appropriate amount of purified water is added and the solution gently mixed. If any water-soluble additives are included, these may be added first as part of the pre-concentrate, or added later to the aqueous dispersion, as desired. As noted above, the hydrophobic therapeutic agent can be present in a first amount solubilized by the carrier, and a second amount suspended (not solubilized) in the carrier, as desired. It should be emphasized that the order of addition of the various components is not generally important and may be changed as convenient.

In another aspect, the present invention relates to a novel method of preparing a pharmaceutical composition of an ionizable hydrophobic therapeutic agent. The method includes the steps of: (I) providing a pharmaceutical composition having an ionizable hydrophobic therapeutic agent and a carrier which includes an ionizing agent and a surfactant; and (II) providing a neutralizing agent to neutralize at least a portion of the ionizing agent.

The pharmaceutical composition provided in step (I) can be any of the pharmaceutical compositions described herein. Preferably, the composition has greater than about 1.5 mole equivalents of ionizing agent per mole of ionizable functional group, although this concentration is not required.

The neutralizing agent provided in step (II) can be any of the pharmaceutically acceptable acids or bases described above. Of course, if the ionizing agent is an acid, the neutralizing agent is a base, and vice versa. Any amount of neutralizing agent that neutralizes at least a portion of the ionizing agent can be used. Preferably, the amount of neutralizing agent used is an amount sufficient to neutralize the ionizing agent so that the amount of ionizing agent is about 0.1 to about 1.5 mole equivalents per mole of ionizable functional group, based on the amounts of ionizing agent and ionizable functional groups present before reaction with each other, but after reaction of the ionizing agent and the neutralizing agent. More preferably, the neutralizing agent is used in an amount sufficient to neutralize the ionizing agent so that the amount of ionizing agent is about 0.1 to about 1.0 mole equivalents per mole of ionizable functional group.

For some applications, particularly for preparing pharmaceutical compositions in a gelatin capsule dosage form, it may be desirable to use a smaller amount of ionizing agent, in the range of about 0.1 to about 1.5 mole equivalents, preferably about 0.1 to about 1.0 mole equivalents, per mole of ionizable functional group, based on pre-reaction amounts. This lower amount of ionizing agent provides better compatibility with the gelatin capsule dosage form. However, as discussed above, it is desirable to use an excess of ionizing agent to promote increased solubilization and ease of preparation of solubilized compositions. Thus, in the present method, an excess of ionizing agent can be used in preparing a composition, and a portion of the excess can then be neutralized to provide a composition more suited to certain dosage forms, particularly gelatin capsule dosage forms.

The amount of neutralizing agent used is defined in such a way as to make the relative amounts of ionizing agent and ionizable functional groups in the present method consistent with the description above. Thus, it is convenient to define the amount of ionizing agent as the pre-reaction amount, before the acid-base reaction with the ionizable functional groups, as described above. In order to keep this convention, the amount of neutralizing agent is defined by adopting the following convenient fiction: first, the neutralizing agent is imagined to react with the ionizing agent, to neutralize a portion of the ionizing agent; then, the remaining ionizing agent is imagined to react with the ionizable functional groups, to ionize at least a portion of the ionizable functional groups. Thus, in a preferred embodiment, the amount of neutralizing agent is selected so that after the first step of the hypothetical two-step ionization—i.e., the neutralization reaction between the neutralizing agent and the ionizing agent—the amount of ionizing agent available in the second step is about 0.1 to about 1.5 mole equivalents, preferably about 0.1 to about 1.0 mole equivalents, per mole of ionizable functional group.

As a specific example, if the amount of ionizable functional groups is 1.0 mole, and the amount of ionizing agent used is 10.0 moles, then to achieve a concentration of ionizing agent within a pre-reaction range of 0.1 to 1.5 moles, an amount of neutralizing agent sufficient to neutralize from 8.5 to 9.9 moles of ionizing agent is used. In the hypothetical first neutralization step, the 8.5 to 9.9 mole equivalents of neutralizing agent neutralizes 8.5 to 9.9 moles of the ionization agent, leaving 0.1 to 1.5 moles unreacted. Thus, the amount of ionizing agent hypothetically present before reaction with the ionizable functional group is 0.1 to 1.5 moles. It should be apparent that the actual reaction sequence does not follow this hypothetical scheme, but such a scheme merely provides a simple stoichiometric reference frame.

9. Methods of Treating an Animal

In another aspect, the present invention relates to methods of improving delivery of ionizable hydrophobic therapeutic agents in an animal by administering to the animal a dosage form of the pharmaceutical compositions described herein. Preferably the animal is a mammal, and more preferably, a human. It is believed that the pharmaceutical compositions of the present invention when administered to an animal enable the ionizable hydrophobic therapeutic agent contained therein to be delivered to the absorption site with less or no precipitation of the therapeutic agent, resulting in better bioavailability.

In use, the methods and compositions of the present invention provide a number of important advantages, including:

Robustness to Dilution: The compositions of the present invention are unexpectedly robust to dilution in media simulating the conditions normally encountered in the gastrointestinal and intestinal tracts. Precipitation of the therapeutic agent is minimal, and is delayed upon administration, due to the protective effects of the surfactant and optional solubilizer components.

Improved Delivery: The compositions of the present invention unexpectedly provide improved delivery of the therapeutic agent to the absorption site, by minimizing precipitation. This improved delivery is believed to result in better bioavailability of the therapeutic agent.

Less Dependence Upon Other Factors: The compositions of the present invention enable the absorption of the hydrophobic therapeutic agent independent of wetting/dissolution rates, and less dependent upon meal, gastro-intestinal contents, and bilary secretions, by maintaining the therapeutic agent in solubilized form upon administration. In addition, when the optional triglyceride component is absent, dependence upon the rate of lipolysis is reduced or eliminated.

High Loading Capacity: The compositions of the present invention provide high loading capacity for ionizable hydrophobic therapeutic agents. The surfactants and optional triglycerides and solubilizers interact with the hydrophobic therapeutic agent to unexpectedly solubilize large amounts of therapeutic agent. In addition, when an additional non-solubilized amount of therapeutic agent is included, still larger therapeutic agent concentrations can be achieved, while still preserving the advantages in stability and bioavailability of the solubilized therapeutic agent.

Ease of Preparation: The methods of the present invention provide compositions in which the hydrophobic therapeutic agent is readily solubilized, thereby conserving expensive manufacturing and personnel resources.

Versatility: Because the compositions of the present invention can effectively make use of a wide variety of different surfactants, solubilizers and triglycerides to solubilize a wide variety of ionizable hydrophobic therapeutic agents, compositions can be carefully tailored to the polarity and functionality of the therapeutic agents, without compromising the improved solubilization, delivery, and other advantages as described above.

These and other advantages of the present invention, as well as aspects of preferred embodiments, are illustrated more fully in the Examples which follow.

EXAMPLES

Example 1

Carrier Formulations

Carrier formulations can be prepared by simple mixing of the desired components, with gentle heating if desired. Table 20 contains examples of carrier formulations according to the present invention, using a wide variety of surfactants, surfactant mixtures, solubilizers, and other components. The desired amount of ionizable hydrophobic therapeutic agent is included in the carrier to produce a pharmaceutical composition.

TABLE 20

Carrier Formulations

| Formulation # | Composition (g) | |
|---|---|---|
| 1 | Concentrated Hydrochloric Acid | 0.005 |
|  | Cremophor RH-40 | 0.650 |
|  | Span 80 | 0.300 |
|  | Sterotex NF | 0.050 |
| 2 | Concentrated Hydrochloric Acid | 0.010 |
|  | Solulan C-24 | 0.700 |
|  | Crovol M-40 | 0.250 |
|  | Soybean Oil USP | 0.050 |
| 3 | Methanesulfonic Acid | 0.020 |
|  | Incrocas 35 | 0.750 |
|  | ARLACEL 186 | 0.150 |
|  | Captex 300 | 0.100 |
| 4 | Methanesulfonic Acid | 0.020 |
|  | Crovol M-70 | 0.800 |
|  | Imwitor 988 | 0.200 |
| 5 | Concentrated Hydrochloric Acid | 0.015 |
|  | Incrocas 35 | 0.600 |
|  | Myvacet 9-45 | 0.400 |
| 6 | Concentrated Phosphoric Acid | 0.050 |
|  | Poloxamer 188 | 0.850 |
|  | Labrafil M2125CS | 0.150 |
| 7 | Concentrated Phosphoric Acid | 0.030 |
|  | Cremophor EL-P | 0.830 |
|  | Peceol | 0.170 |
| 8 | Citric Acid (aq.) | 0.050 |
|  | Crodet O40 | 0.680 |
|  | Plurol Oleique | 0.320 |
| 9 | Glacial Acetic Acid | 0.100 |
|  | Tween 80 | 0.750 |
|  | Lauroglycol FCC | 0.150 |
| 10 | Glacial Acetic Acid | 0.050 |
|  | Brij 35 | 0.750 |
|  | Labrasol | 0.200 |
| 11 | Concentrated Hydrochloric Acid | 0.010 |
|  | Cremophor EL | 0.300 |
|  | Labrasol | 0.300 |
|  | Capmul MCM | 0.400 |
| 12 | Concentrated Hydrochloric Acid | 0.020 |
|  | Tween 20 | 0.660 |
|  | ARLACEL 186 | 0.170 |
|  | Sodium Taurocholate | 0.170 |
| 13 | Concentrated Hydrochloric Acid | 0.005 |
|  | Cremophor RH-40 | 0.500 |
|  | Captex 200 | 0.200 |
|  | Captex 810 | 0.100 |
|  | PEG 200 | 0.200 |
| 14 | Concentrated Hydrochloric Acid | 0.010 |
|  | Cremophor RH-40 | 0.600 |
|  | Crovol M-40 | 0.200 |
|  | Hydrokote AP5 | 0.050 |
|  | Ethanol | 0.150 |
| 15 | Methanesulfonic Acid | 0.020 |
|  | Incrocas 35 | 0.650 |
|  | ARLACEL 186 | 0.120 |
|  | PEG 400 | 0.230 |
| 16 | Methanesulfonic Acid | 0.020 |
|  | Crovol M-70 | 0.650 |
|  | Imwitor 988 | 0.150 |
|  | Polyethylene Glycol | 0.200 |
| 17 | Concentrated Hydrochloric Acid | 0.015 |
|  | Incrocas 35 | 0.500 |
|  | Myvacet 9-45 | 0.350 |
|  | Methoxy PEG 400 | 0.150 |
| 18 | Concentrated Phosphoric Acid | 0.050 |
|  | Crovol M-70 | 0.750 |
|  | Labrafil M2125CS | 0.130 |
|  | Triacetin | 0.120 |
| 19 | Concentrated Phosphoric Acid | 0.030 |
|  | Cremophor EL-P | 0.750 |
|  | Peceol | 0.150 |
|  | Dimethyl Isosorbide | 0.100 |
| 20 | Concentrated Phosphoric Acid | 0.050 |
|  | Tween 20 | 0.580 |
|  | Plurol Oleique | 0.210 |
|  | Transcutol | 0.210 |

TABLE 20-continued

Carrier Formulations

| Formulation # | Composition (g) | |
|---|---|---|
| 21 | Concentrated Phosphoric Acid | 0.050 |
| | Tween 80 | 0.670 |
| | Lauroglycol FCC | 0.170 |
| | Glycofurol | 0.160 |
| 22 | Concentrated Phosphoric Acid | 0.050 |
| | Tween-20 | 0.300 |
| | ARLACEL 186 | 0.150 |
| | Propylene Glycol | 0.500 |
| 23 | Concentrated Hydrochloric Acid | 0.020 |
| | Cremophor RH-40 | 0.450 |
| | ARLACEL 186 | 0.100 |
| | Sodium Taurocholate | 0.300 |
| | Ethanol | 0.150 |
| 24 | Concentrated Hydrochloric Acid | 0.020 |
| | Cremophor RH-40 | 0.650 |
| | ARLACEL 186 | 0.150 |
| | Sodium Dodecyl Sulfate | 0.100 |
| | PEG 400 | 0.100 |
| 25 | Concentrated Hydrochloric Acid | 0.010 |
| | Tagat L2 | 0.450 |
| | Crovol A-40 | 0.250 |
| | Sodium Docusate | 0.150 |
| | 2-pyrrolidone | 0.150 |
| 26 | Concentrated Hydrochloric Acid | 0.010 |
| | Poloxamer 108 | 0.450 |
| | Span 80 | 0.250 |
| | Sodium Docusate | 0.150 |
| | Ethyl Oleate | 0.150 |
| 27 | Concentrated Phosphoric Acid | 0.025 |
| | Tween-20 | 0.300 |
| | ARLACEL 186 | 0.200 |
| | Sodium Taurocholeate | 0.150 |
| | Propylene Glycol | 0.300 |
| 28 | Concentrated Hydrochloric Acid | 0.025 |
| | Tween-20 | 0.300 |
| | ARLACEL 186 | 0.175 |
| | Sodium Taurocholate | 0.150 |
| | Propylene Glycol | 0.300 |
| 29 | Concentrated Hydrochloric Acid | 0.025 |
| | Tween-20 | 0.300 |
| | ARLACEL 186 | 0.150 |
| | Sodium Taurocholate | 0.150 |
| | Propylene Glycol | 0.325 |
| 30 | Concentrated Phosphoric Acid | 0.100 |
| | Tween-20 | 0.300 |
| | Sodium Taurocholate | 0.100 |
| | Glycofurol | 0.500 |
| | Ethanol | 0.100 |
| 31 | Concentrated Phosphoric Acid | 0.100 |
| | Tween-20 | 0.300 |
| | ARLACEL 186 | 0.050 |
| | Sodium Taurocholate | 0.100 |
| | Glycofurol | 0.500 |
| | Ethanol | 0.100 |
| 32 | Concentrated Hydrochloric Acid | 0.025 |
| | Incrocas 40 | 0.500 |
| | Crovol M-40 | 0.100 |
| | Captex 355 | 0.100 |
| | PEG 400 | 0.250 |
| | Sodium Hydroxide (5N aq.) | 0.020 |
| 33 | Methanesulfonic Acid | 0.020 |
| | Incrocas 35 | 0.830 |
| | Imwitor 742 | 0.170 |
| | Sodium Hydroxide (5N aq.) | 0.010 |
| 34 | Methanesulfonic Acid | 0.020 |
| | Crovol M-70 | 0.800 |
| | Imwitor 988 | 0.200 |
| | Potassium Hydroxide (5N aq.) | 0.010 |
| 35 | Concentrated Hydrochloric Acid | 0.025 |
| | Crodesta F-160 | 0.550 |
| | Myvacet 9-45 | 0.350 |
| | Methoxy PEG 400 | 0.100 |
| | Triethylamine | 0.005 |
| 36 | Concentrated Phosphoric Acid | 0.050 |
| | Poloxamer 188 | 0.750 |
| | Labrafil M2125CS | 0.150 |
| | Glycofurol | 0.100 |
| | Concentrated Ammonium Hydroxide | 0.010 |
| 37 | Concentrated Phosphoric Acid | 0.030 |
| | Cremophor EL-P | 0.830 |
| | Peceol | 0.170 |
| | Concentrated Sodium Acetate (aq.) | 0.010 |
| 38 | Sodium Hydroxide (5N aq.) | 0.010 |
| | Crovol M-70 | 0.650 |
| | Labrafil M2125CS | 0.250 |
| | Softisan 378 | 0.100 |
| 39 | Sodium Hydroxide (5N aq.) | 0.010 |
| | Incrocas 40 | 0.800 |
| | ARLACEL 186 | 0.150 |
| | Corn Oil NF | 0.050 |
| 40 | Sodium Hydroxide (5N aq.) | 0.005 |
| | Tagat TO | 0.650 |
| | Imwitor 988 | 0.250 |
| | Miglyol 810 | 0.100 |
| 41 | Sodium Hydroxide (10N aq.) | 0.010 |
| | Cremophor RH-40 | 0.700 |
| | Volpo 3 | 0.300 |
| 42 | Sodium Hydroxide (10N aq.) | 0.005 |
| | Cremophor EL-P | 0.200 |
| | Labrasol | 0.400 |
| | Nikkol Decaglyn 3-O | 0.400 |
| 43 | Concentrated Sodium Acetate (aq.) | 0.030 |
| | Poloxamer 108 | 0.850 |
| | Capmul GMO-K | 0.150 |
| 44 | Sodium Hydroxide (10N aq.) | 0.008 |
| | Glycerox L | 0.730 |
| | Myvacet 9-45 | 0.270 |
| 45 | Sodium Hydroxide (10N aq.) | 0.008 |
| | Tagat L2 | 0.680 |
| | Brij 30 | 0.320 |
| 46 | Potassium Hydroxide (5N aq.) | 0.020 |
| | Tween 20 | 0.750 |
| | Drewpol 6-1-O | 0.150 |
| 47 | Potassium Hydroxide (5N aq.) | 0.020 |
| | Tween 80 | 0.750 |
| | Maisine 35-I | 0.200 |
| 48 | Potassium Hydroxide (5N aq.) | 0.010 |
| | Kessco PEG 1000 ML | 0.300 |
| | Labrasol | 0.300 |
| | Span 20 | 0.400 |
| 49 | Potassium Hydroxide (5N aq.) | 0.010 |
| | Kessco PEG 1000 MO | 0.660 |
| | Plurol Oleique | 0.170 |
| | Sodium Taurocholate | 0.170 |
| 50 | Potassium Hydroxide (10N aq.) | 0.010 |
| | Myrj 51 | 0.540 |
| | Kessco PEG 300 DL | 0.200 |
| | Corn oil NF | 0.060 |
| | PEG 200 | 0.200 |
| 51 | Potassium Hydroxide (10N aq.) | 0.010 |
| | Kessco PEG 1540 DL | 0.600 |
| | Crovol A-40 | 0.150 |
| | Castorwax | 0.050 |
| | Ethanol | 0.200 |
| 52 | Potassium Hydroxide (10N aq.) | 0.005 |
| | Kessco PEG 1540DO | 0.650 |
| | Span 80 | 0.120 |
| | PEG 400 | 0.230 |
| 53 | Ethanolamine | 0.005 |
| | Gelucire 44/14 | 0.650 |
| | Captex 200 | 0.150 |
| | Polyethylene Glycol | 0.200 |
| 54 | Ethanolamine | 0.005 |
| | Gelucire 50/13 | 0.500 |
| | Kessco PEG 300 DL | 0.350 |
| | Methoxy PEG 400 | 0.150 |

TABLE 20-continued

Carrier Formulations

| Formulation # | Composition (g) | |
|---|---|---|
| 55 | Triethylamine | 0.005 |
|  | Nikkol Decaglyn 1-L | 0.550 |
|  | Crovol M-40 | 0.330 |
|  | Triacetin | 0.120 |
| 56 | Diisopropylethylamine | 0.005 |
|  | Nikkol Decaglyn 1-O | 0.650 |
|  | Capmul MCM | 0.250 |
|  | Dimethyl Isosorbide | 0.100 |
| 57 | Triethanolamine | 0.005 |
|  | Solulan C-24 | 0.580 |
|  | Lauroglycol FCC | 0.210 |
|  | Transcutol | 0.210 |
| 58 | Ammonium Hydroxide | 0.010 |
|  | Nikkol DHC | 0.670 |
|  | Nikkol TMGO-5 | 0.170 |
|  | Glycofurol | 0.160 |
| 59 | Concentrated Ammonium Acetate (aq.) | 0.050 |
|  | Nikkol BPS-30 | 0.300 |
|  | PEG-6 Castor Oil | 0.150 |
|  | Propylene Glycol | 0.500 |
| 60 | Concentrated Sodium Acetate (aq.) | 0.050 |
|  | Cremophor RH-40 | 0.350 |
|  | Capmul MCM | 0.300 |
|  | Sodium Taurocholate | 0.200 |
|  | Ethanol | 0.100 |
| 61 | Lysine Ethyl Ester | 0.010 |
|  | Poloxamer 188 | 0.650 |
|  | Peceol | 0.150 |
|  | Sodium Dodecyl Sulfate | 0.100 |
|  | PEG 400 | 0.100 |
| 62 | Concentrated Sodium Citrate (aq.) | 0.010 |
|  | Cremophor EL | 0.450 |
|  | Crovol M-40 | 0.250 |
|  | Sodium Docusate | 0.150 |
|  | 2-pyrrolidone | 0.150 |
| 63 | Sodium Hydroxide (10N aq.) | 0.010 |
|  | Softigen 767 | 0.450 |
|  | Imwitor 742 | 0.250 |
|  | Sodium Docusate | 0.150 |
|  | Ethyl Oleate | 0.150 |
| 64 | Concentrated Potassium Phosphate (aq.) | 0.025 |
|  | Poloxamer 407 | 0.300 |
|  | Mapeg 200 ML | 0.200 |
|  | Sodium Taurocholate | 0.150 |
|  | Propylene Glycol | 0.300 |
| 65 | Triethylamine | 0.007 |
|  | Tween-20 | 0.300 |
|  | ARLACEL 186 | 0.100 |
|  | Sodium Taurocholate | 0.100 |
|  | Propylene Glycol | 0.500 |
|  | Butylated Hydroxytoluene | 0.010 |
|  | Edetate Disodium | 0.001 |
| 66 | Sodium Hydroxide (5N aq.) | 0.020 |
|  | Tween-20 | 0.300 |
|  | ARLACEL 186 | 0.100 |
|  | Sodium Taurocholate | 0.100 |
|  | Propylene Glycol | 0.500 |
|  | Butylated Hydroxytoluene | 0.010 |
|  | Edetate Disodium | 0.001 |
| 67 | Sodium Hydroxide (10N aq.) | 0.020 |
|  | Tween 20 | 0.500 |
|  | Peceol | 0.100 |
|  | Pureco 76 | 0.050 |
|  | PEG 400 | 0.300 |
|  | Concentrated Hydrochloric Acid | 0.005 |
| 68 | Potassium Hydroxide (5N aq.) | 0.025 |
|  | Labrasol | 0.830 |
|  | Lauroglycol FCC | 0.170 |
|  | Concentrated Phosphoric Acid | 0.010 |
| 69 | Methanesulfonic Acid | 0.020 |
|  | Crovol M-70 | 0.800 |
|  | Imwitor 988 | 0.200 |
|  | Potassium Hydroxide (5N aq.) | 0.010 |
| 70 | Triethylamine | 0.025 |
|  | Crovol K-70 | 0.550 |

TABLE 20-continued

Carrier Formulations

| Formulation # | Composition (g) | |
|---|---|---|
|  | Captex 100 | 0.350 |
|  | Methoxy PEG 400 | 0.100 |
|  | Concentrated Hydrochloric Acid | 0.005 |

Example 2

Stability of Solutions of Itraconazole upon Dilution in Simulated Gastric Fluid

Carriers were prepared according to Example 1, using the specific carrier formulations shown in Example 1 as Nos. 27–31. From 10 to 85 mg of itraconazole was included in the carriers, as indicated in Table 21. An aliquot of each solution of itraconazole was diluted 100-fold in an enzyme-free simulated gastric fluid (SGF). The diluent was incubated at 37° C. while being tumbled on a rotor. At the indicated time during the incubation, the amount of itraconazole remaining solubilized in the diluent was determined by drug specific HPLC, as a measure of the stability of these formulations in the SGF. A dosage form of a commercial oral itraconazole product, SPORANOX® (a 10 mg/mL drink solution) was also tested under the same experimental conditions, for comparison.

TABLE 21

Stability of Compositions in SGF

| Formulation | Itraconazole (mg/mL) | % Itraconazole Remaining Solubilized in the Diluent After: | | | | |
|---|---|---|---|---|---|---|
|  |  | 1 hr | 2 hr | 4 hr | 6 hr | 24 hr |
| 27 | 30 | 71.9 | 69.9 | 71.5 | 65.6 |  |
| 27 | 85 | 41.4 | 45.8 | 47.3 | 45.2 | 6.4 |
| 28 | 30 |  | 101.8 | 96.5 | 95.4 | 88.7 |
| 28 | 40 |  | 72.2 | 74.7 | 79.9 | 78.9 |
| 28 | 50 |  | 54.1 | 58.8 | 67.7 | 48.3 |
| 29 | 30 |  |  | 93.5 |  | 94.5 |
| 29 | 50 |  |  | 54.9 |  | 64.7 |
| 30 | 10 | 92.5 | 95.8 | 89.3 | 91.6 | 78.6 |
| 30 | 20 | 94.4 | 89.6 | 78.0 | 78.4 | 66.2 |
| 30 | 30 | 84.3 | 78.4 | 71.0 | 66.9 | 69.1 |
| 31 | 10 | 99.3 | 94.3 | 86.5 | 92.4 | 78.5 |
| 31 | 30 | 99.7 | 98.1 | 91.7 | 94.1 | 87.5 |
| SPORANOX ® | 10 | 104.8 | 104.8 | 105.0 | 98.8 | 94.2 |

Example 3

Stability of Solutions of Itraconazole upon Dilution in Simulated Intestinal Fluid Carriers were prepared according to Example 1, using the specific carrier formulations shown in Example 1 as Nos. 27–29 and 3 1. From 10 to 85 mg of itraconazole was included in the carriers, as indicated in Table 22. An aliquot of each solution of itraconazole was diluted 100-fold in an enzyme-free simulated intestinal fluid (SIF). The diluent was incubated at 37° C. while being tumbled on a rotor. At the indicated time during the incubation, the amount of itraconazole remaining solubilized in the diluent was determined by HPLC, as a measure of the stability of these formulations in the SIF. Two dosage forms of a commercial oral itraconazole product, SPORANOX® (a 10 mg/mL drink solution and a 100 mg hard gelatin capsule) were also tested under the same experimental conditions, for comparison.

TABLE 22

Stability of Compositions in SIF

| Formulation | Itraconazole (mg/mL) | % Itraconazole Remaining Solubilized in the Diluent After: | | | | |
|---|---|---|---|---|---|---|
| | | 1 hr | 2 hr | 4 hr | 6 hr | 24 hr |
| 27 | 30 | 90.9 | 91.1 | 88.9 | | 60.2 |
| 27 | 85 | 26.8 | 15.3 | 5.5 | | |
| 28 | 10 | 86.1 | 85.8 | 81.5 | | 62.6 |
| 28 | 30 | 81.8 | 85.8 | 83.1 | | 3.5 |
| 28 | 40 | 82.1 | 83.6 | 81.9 | | 1.8 |
| 29 | 30 | 77.6 | 77.1 | 71.0 | | 1.7 |
| 31 | 10 | | 29.7 | 25.2 | n. d. | |
| 31 | 30 | | 30.7 | 29.3 | 18.4 | |
| SPORANOX | 10 | 2.2 | 6.1 | 4.1 | | n. d. |
| SPORANOX | 100 mg capsule | n. d. | n. d. | n. d. | | | n. d.: not detectable

Example 4
Stability of Solutions of Tretinoin upon Dilution in Simulated Gastric Fluid Example 2 was repeated, but using tretinoin as the ionizable hydrophobic therapeutic agent and formulation Nos. 65 and 66 as the carrier. The results are shown in Table 23.

TABLE 23

Stability of Compositions in SGF

| Formulation | Tretinoin (mg/mL) | % Tretinoin Remaining Solubilized in the Diluent After 3 hr. |
|---|---|---|
| 65 | 10 | 84.5 |
| 66 | 10 | 49.3 |

Example 5
Stability of Solutions of Tretinoin upon Dilution in Simulated Intestinal Fluid Example 4 was repeated in simulated intestinal fluid instead of simulated gastric fluid. The results are shown in Table 24.

TABLE 24

Stability of Compositions in SIF

| Formulation | Tretinoin (mg/mL) | % Tretinoin Remaining Solubilized in the Diluent After 3 hr. |
|---|---|---|
| 65 | 10 | 92.5 |
| 66 | 10 | 53.7 |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A pharmaceutical composition comprising:
    (a) a hydrophobic theraputic agent having at least one ionizable functional group and an intrinsic water solubility of less than about 1% by weight; and
    (b) a carrier comprising:
        (i) an ionizing agent capable of ionizing the at least one ionizable functional group, wherein the ionizing agent is present in an amount of at least about 0.1 mole equivalents per mole of the at least one functional group;
        (ii) a surfactant selected from the group consisting of non-ionic hydrophilic surfactants having an HLB value greater than or equal to about 10, ionic hydrophilic surfactants, hydrophobic surfactants having an HLB value less than 10, and mixtures thereof; and
        (iii) a triglyceride.

2. The pharmaceutical composition of claim 1, wherein the at least one ionizable functional group is an acidic functional group, and the ionizing agent is a pharmaceutically acceptable base.

3. The pharmaceutical composition of claim 2, wherein the acidic functional group is selected from the group consisting of carboxylic acids, imidazolidinediones, thiazolidinediones, pyrimidinetriones, hydroxyheteroaromatics, phenols, phosphoric acids, sulfuric acids, sulfonic acids, sulfonamides, aminosulfones, sulfonylureas, tetrazoles and thiols.

4. The pharmaceutical composition of claim 2, wherein the hydrophobic therapeutic agent is selected from the group consisting of acetazolamide, acetohexamide, acrivastine, alatrofloxacin, albuterol, alclofenac, aloxiprin, alprostadil, amodiaquine, amphotericin, amylobarbital, aspirin, atorvastatin, atovaquone, baclofen, barbital, benazepril, bezafibrate, bromfenac, bumetanide, butobarbital, candesartan, capsaicin, captopril, cefazolin, celecoxib, cephadrine, cephalexin, cerivastatin, cetrizine, chlorambucil, chlorothiazide, chlorpropamide, chlorthalidone, cinoxacin, ciprofloxacin, clinofibrate, cloxacillin, cromoglicate, cromolyn, dantrolene, dichlorophen, diclofenac, dicloxacillin, dicumarol, diflunisal, dimenhydrinate, divalproex, docusate, dronabinol, enoximone, enalapril, enoxacin, enrofloxacin, epalrestat, eposartan, essential fatty acids, estramustine, ethacrynic acid, ethotoin, etodolac, etoposide, fenbufen, fenoprofen, fexofenadine, fluconazole, flurbiprofen, fluvastatin, fosinopril, fosphenytoin, fumagillin, furosemide, gabapentin, gemfibrozil, gliclazide, glipizide, glybenclamide, glyburide, glimepiride, grepafloxacin, ibufenac, ibuprofen, imipenem, indomethacin, irbesartan, isotretinoin, ketoprofen, ketorolac, lamotrigine, levofloxacin, levothyroxine, lisinopril, lomefloxacin, losartan, lovastatin, meclofenamic acid, mefenamic acid, mesalamine, methotrexate, metolazone, montelukast, nalidixic acid, naproxen, natamycin, nimesulide, nitrofurantoin, non-essential fatty acids, norfloxacin, nystatin, ofloxacin, oxacillin, oxaprozin, oxyphenbutazone, penicillins, pentobarbital, perfloxacin, phenobarbital, phenytoin, pioglitazone, piroxicam, pramipexol, pranlukast, pravastatin, probenecid, probucol, propofol, propylthiouracil, quinapril, rabeprazole, repaglinide, rifampin, rifapentine, sparfloxacin, sulfabenzamide, sulfacetamide, sulfadiazine, sulfadoxine, sulfamerazine, sulfamethoxazole, sulfafurazole, sulfapyridine, sulfasalazine, sulindac, sulphasalazine, sulthiame, telmisartan, teniposide, terbutaline, tetrahydrocannabinol, tirofiban, tolazamide, tolbutamide, tolcapone, tolmetin, tretinoin, troglitazone, trovafloxacin, undecenoic acid, ursodeoxycholic acid, valproic acid, valsartan, vancomycin, verteporfin, vigabatrin, vitamin K-S (II), zafirlukast, and pharmaceutically acceptable salts thereof.

5. The pharmaceutical composition of claim 4, wherein the hydrophobic therapeutic agent is selected from the group consisting of acetohexamide, acrivastine, alatrofloxacin, albuterol, alclofenac, amodiaquine, amphotericin, aspirin, atorvastatin, atovaquone, baclofen, benazepril, bezafibrate, bromfenac, butobarbital, candesartan, capsaicin, captopril, celecoxib, cerivastatin, cetrizine, chlorambucil, chlorpropamide, chlorthalidone, clinofibrate, cinoxacin, ciprofloxacin, clinofibrate, cloxacillin, cromoglicate, cromolyn, dantrolene, diclofenac, dicumarol, divalproex, docusate, dronabinol, enalapril, enoxacin, epalrestat, eposartan, etodolac, etoposide, fenbufen, fenoprofen, fexofenadine, fluconazole, flurbiprofen, fluvastatin, fosphenytoin, fumagillin, gabapentin, gemfibrozil, gliclazide, glipizide, glyburide, glimepiride, grepafloxacin, ibufenac, ibuprofen, imipenem, indomethacin, irbesartan, isotretinoin, ketoprofen, ketorolac, lamotrigine, levofloxacin, levothyroxine, lisinopril, lomefloxacin, losartan, lovastatin, mesalamine, methotrexate, montelukast, naproxen, nimesulide, non-essential fatty acids, norfloxacin, ofloxacin, oxaprozin, phenytoin, pioglitazone, piroxicam, pramipexol, pravastatin, probucol, propofol, rabeprazole, repaglinide, rifampin, rifapentine, sparfloxacin, sulfadiazine, sulfamethoxazole, sulfasalazine, sulindac, sulphasalazine, telmisartan, teniposide, terbutaline, tetrahydrocannabinol, tirofiban, tolazamide, tolbutamide, tolcapone, tolmetin, tretinoin, troglitazone, trovafloxacin, undecenoic acid, valproic acid, valsartan, vancomycin, verteporfin, vigabatrin, vitamin K-S (II), zafirlukast, and pharmaceutically acceptable salts thereof.

6. The pharmaceutical composition of claim 5, wherein the hydropeutic agent is selected from the group consisting of acrivastine, alatrofloxacin, albuterol, alclofenac, aspirin, atorvastatin, atovaquone, baclofen, benazepril, bezafibrate, bromfenac, butobarbital, celecoxib, cerivastatin, cetrizine, chlorpropamide, ciprofloxacin, cromoglicate, cromolyn, dantrolene, diclofenac, dicumarol, divalproex, dronabinol, enoxacin, epalrestat, etodolac, etoposide, fenoprofen, fexofenadine, fluconazole, flurbiprofen, fluvastatin, fosphenytoin, gemfibrozil, glipizide, glybunde, glimepiride, grepafloxacin, ibufenac, ibuprofen, isotretinoin, ketoprofen, ketorolac, lamotrigine, levofloxacin, levothyroxine, lomefloxacin, lovastatin, methotrexate, montelukast, naproxen, nimesulide, non-essential fatty acids, norfloxacin, ofloxacin, oxaprozin, phenytoin, pioglitazone, piroxicam, pravastatin, probucol, rabeprazole, repaglinide, rifampin, rifapentine, sulfamethoxazole, sulfasalazine, teniposide, tetrahydrocannabinol, tolcapone, tolmetin, tretinoin, troglitazone, trovafloxacin, valproic acid, vancomycin, vitamin K-S (II), zafirlukast, and pharmaceutically acceptable salts thereof.

7. The pharmaceutical composition of claim 6, wherein the hydrophobic therapeutic agent is selected from the group consisting of alclofenac, aspirin, atorvastatin, atovaquone, benazepril, bromfenac, celecoxib, cromoglicate, cromolyn, diclofenac, dronabinol, epalrestat, etodolac, fexofenadine, flurbiprofen, glimepiride, ibufenac, ibuprofen, isotretinoin, ketorolac, levothyroxine, naproxen, non-essential fatty acids, oxaprozin, phenytoin, pioglitazone, rabeprazole, repaglinide, teniposide, tetrahydrocannabinol, tolmetin, tretinoin, troglitazone, trovafloxacin, vitamin K-S (II), and pharmaceutically acceptable salts thereof.

8. The pharmaceutical composition of claim 2, wherein the base is selected from the group consisting of an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, salts of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, parabromophenylsulfonic acid, propionic acid, p-toluenesulfonic acid, salicylic acid, stearic acid, succinic acid, tannic acid, tartaric acid, thioglycolic acid, toluenesulfonic acid, or uric acid, and mixtures of any of the foregoing.

9. The pharmaceutical composition of claim 1, wherein the at least one ionizable functional group is a basic functional group, and the ionizing agent is a pharmaceutically acceptable acid.

10. The pharmaceutical composition of claim 9, wherein the basic functional group is selected from the group consisting of aliphatic amines, aromatic amines, C-substituted aromatic amines, N-substituted aromatic amines, heterocyclic amines, C-substituted heterocyclic amines and N-substituted heterocyclic amines.

11. The pharmaceutical composition of claim 9, wherein the hydrophobic therapeutic agent is selected from the group consisting of abacavir, acebutolol, acrivastine, alatrofloxacin, albuterol, albendazole, alprazolam, alprenolol, amantadine, amiloride, aminoglutethimide, amiodarone, amitriptyline, amlodipine, amodiaquine, amoxapine, amphetamine, amphotericin, amprenavir, amrinone, amsacrine, astemizole, atenolol, atropine, azathioprine, azelastine, azithromycin, baclofen, benethamine, benidipine, benzhexol, benznidazole, benztropine, biperiden, bisacodyl, bisanthrene, bromazepam, bromocriptine, bromperidol, brompheniramine, brotizolam, bupropion, butenafine, butoconazole, cambendazole, camptothecin, carbinoxamine, cephadrine, cephalexin, cetrizine, cinnarizine, chlorambucil, chlorpheniramine, chlorproguanil, chlordiazepoxide, chlorpromazine, chlorprothixene, chloroquine, cimetidine, ciprofloxacin, cisapride, citalopram, clarithromycin, clemastine, clemizole, clenbuterol, clofazimine, clomiphene, clonazepam, clopidogrel, clozapine, clotiazepam, clotrimazole, codeine, cyclizine, cyproheptadine, dacarbazine, darodipine, decoquinate, delavirdine, demeclocycline, dexamphetamine, dexchlorpheniramine, dexfenfluramine, diamorphine, diazepam, diethylpropion, dihydrocodeine, dihydroergotamine, diltiazem, dimenhydrinate, diphenhydramine, diphenoxylate, diphenylimidazole, diphenylpyraline, dipyridamole, dirithromycin, disopyramide, dolasetron, domperidone, donepezil, doxazosin, doxycycline, droperidol, econazole, efavirenz, ellipticine, enalapril, enoxacin, enrofloxacin, eperisone, ephedrine, ergotamine, erythromycin, ethambutol, ethionamide, ethopropazine, etoperidone, famotidine, felodipine, fenbendazole, fenfluramine, fenoldopam, fentanyl, fexofenadine, flecainide, flucytosine, flunarizine, flunitrazepam, fluopromazine, fluoxetine, fluphenthixol, fluphenthixol decanoate, fluphenazine, fluphenazine decanoate, flurazepam, flurithromycin, frovatriptan, gabapentin, granisetron, grepafloxacin, guanabenz, halofantrine, haloperidol, hyoscyamine, imipenem, indinavir, irinotecan, isoxazole, isradipine, itraconazole, ketoconazole, ketotifen, labetalol, lamivudine, lanosprazole, leflunomide, levofloxacin, lisinopril, lomefloxacin, loperamide, loratadine, lorazepam, lormetazepam, lysuride, mepacrine, maprotiline, mazindol, mebendazole, meclizine, medazepam, mefloquine, melonicam, meptazinol, mercaptopurine, mesalamine, mesoridazine, metformin, methadone, methaqualone, methylphenidate, methylphenobarbital, methysergide, metoclopramide, metoprolol, metronidazole, mianserin, miconazole, midazolam, miglitol, minoxidil, mitomycins, mitoxantrone, molindone, montelukast, morphine, moxifloxacin, nadolol, nalbuphine, naratriptan, natamycin, nefazodone, nelfinavir, nevirapine, nicardipine, nicotine, nifedipine, nimodipine, nimorazole, nisoldipine, nitrazepam, nitrofurazone, nizatidine, norfloxacin, nortriptyline, nystatin, ofloxacin, olanzapine, omeprazole, ondansetron, omidazole, oxamniquine, oxantel, oxatomide, oxazepam, oxfendazole, oxiconazole, oxprenolol, oxybutynin, oxyphencyclimine, paroxetine, pentazocine, pentoxifylline, perchlorperazine, perfloxacin, perphenazine, phenbenzamine, pheniramine, phenoxybenzamine, phentermine, physostigmine, pimozide, pindolol, pizotifen, pramipexol, pranlukast, praziquantel, prazosin, procarbazine, prochlorperazine, proguanil, propranolol, pseudoephedrine, pyrantel, pyrimethamine, quetiapine, quinidine, quinine, raloxifene, ranitidine, remifentanil, repaglinide, reserpine, ricobendazole, rifabutin, rifampin, rifapentine, rimantadine, risperidone, ritonavir, rizatriptan, ropinirole, rosiglitazone, roxaditine, roxithromycin, salbutamol, saquinavir, selegiline, sertraline, sibutramine, sildenafil, sparfloxacin, spiramycins, stavudine, sulconazole, sulphasalazine, sulpiride, sumatriptan, tacrine, tamoxifen, tamsulosin, temazepam, terazosin, terbinafine, terbutaline, terconazole, terfenadine, tetramisole, thiabendazole, thioguanine, thioridazine, tiagabine, ticlopidine, timolol, tinidazole, tioconazole, tirofiban, tizanidine, tolterodine, topotecan, toremifene, tramadol, trazodone, triamterene, triazolam, trifluoperazine, trimethoprim, trimipramine, tromethamine, tropicamide, trovafloxacin, vancomycin, venlafaxine, vigabatrin, vinblastine, vincristine, vinorelbine, vitamin $K_5$, vitamin $K_6$, vitamin $K_7$, zafirlukast, zolmitriptan, zolpidem, zopiclone, and pharmaceutically acceptable salts thereof.

12. The pharmaceutical composition of claim 11, wherein the hydrophobic therapeutic agent is selected from the group consisting of abacavir, acebutolol, acrivastine, alatrofloxacin, albendazole, albuterol, alprazolam, amiodarone, amlodipine, amodiaquine, amphetamine, amphotericin, amprenavir, astemizole, atenolol, azathioprine, azelastine, azithromycin, baclofen, benztropine, bisacodyl, bromazepam, bromperidol, brompheniramine, bupropion, butenafine, butoconazole, cambendazole, camptothecin, carbinoxamine, cetrizine, cinnarizine, chlorpheniramine, chlorambucil, chlorpromazine, cimetidine, ciprofloxacin, cisapride, citalopram, clarithromycin, clemastine, clemizole, clomiphene, clonazepam, clopidogrel, clozapine, clotiazepam, clotrimazole, codeine, cyclizine, delavirdine, dexamphetamine, dexchlorpheniramine, diamorphine, diazepam, diethylpropion, dihydrocodeine, dihydroergotamine, diltiazem, diphenhydramine, diphenylimidazole, diphenylpyraline, dipyridamole, dirithromycin, disopyramide, dolasetron, domperidone, donepezil, doxazosin, droperidol, econazole, efavirenz, ellipticine, enalapril, enoxacin, eperisone, ergotamine, famotidine, felodipine, fenfluramine, fenoldopam, fexofenadine, fentanyl, flecainide, flunarizine, fluopromazine, fluoxetine, frovatriptan, gabapentin, granisetron, halofantrine, imipenem, indinavir, irinotecan, isoxazole, isradipine, itraconazole, ketoconazole, ketotifen, labetalol, lamivudine, lanosprazole, leflunomide, levofloxacin, lisinopril, lomefloxacin, loperamide, loratadine, lorazepam, lormetazepam, mazindol, mebendazole, mefloquine, mercaptopurine, mesalamine, metformin, methadone, methaqualone, methylphenidate, methysergide, metoclopramide, metoprolol, metronidazole, miconazole, midazolam, miglitol, minoxidil, mitoxantrone, montelukast, naratriptan, nelfinavir, nevirapine, nicardipine, nicotine, nifedipine, nimodipine, nimorazole, nisoldipine, nizatidine, norfloxacin, ofloxacin, olanzapine, omeprazole, ondansetron, oxamniquine, oxiconazole, paroxetine, perchlorperazine, phenbenzamine, pheniramine, phentermine, physostigmine, pizotifen, pramipexol, prazosin, prochlorperazine, pseudoephedrine, quetiapine, quinidine, raloxifene, ranitidine, remifentanil, repaglinide, rifabutin, rifampin, rifapentine, rimantadine, risperidone, ritonavir, rizatriptan, rosiglitazone, roxaditine, saquinavir, sibutramine, sildenafil, sparfloxacin, stavudine, sulphasalazine, sumatriptan, tacrine, tamoxifen, tamsulosin, terazosin, terbinafine, terbutaline, terconazole, terfenadine, tiagabine, ticlopidine, tinidazole, tioconazole, tirofiban, tizanidine, tolterodine, topotecan, toremifene, tramadol, trazodone, trovafloxacin, vancomycin, venlafaxine, vigabatrin, vinblastine, vincristine, vinorelbine, vitamin $K_5$, vitamin $K_6$, vitamin $K_7$, zafirlukast, zolmitriptan, zolpidem, zopiclone, and pharmaceutically acceptable salts thereof.

13. The pharmaceutical composition of claim 12, wherein the hydrophobic therapeutic agent is selected from the group consisting of abacavir, acrivastine, alatrofloxacin, albuterol, amiodarone, amlodipine, amphetamine, amprenavir, astemizole, atenolol, azathioprine, azelastine, azithromycin, baclofen, benztropine, bisacodyl, bromazepam, bromperidol, brompheniramine, bupropion, butenafine, butoconazole, cambendazole, camptothecin, carbinoxamine, cetrizine, cinnarizine, chlorpheniramine, chlorpromazine, cimetidine, ciprofloxacin, cisapride, clarithromycin, clemastine, clemizole, clonazepam, clopidogrel, clotrimazole, codeine, dexchlorpheniramine, dihydrocodeine, dihydroergotamine, diphenhydramine, diphenylimidazole, diphenylpyraline, dirithromycin, dolasetron, domperidone, doxazosin, econazole, efavirenz, ellipticine, enoxacin, eperisone, ergotamine, famotidine, fenoldopam, fentanyl, fexofenadine, flunarizine, fluoxetine, frovatriptan, granisetron, grepafloxacin, halofantrine, indinavir, irinotecan, isradipine, itraconazole, ketoconazole, ketotifen, lamivudine, lanosprazole, leflunomide, levofloxacin, loperamide, loratadine, metformin, methadone, methylphenidate, methysergide, metronidazole, miconazole, midazolam, miglitol, mitoxantrone, montelukast, naratriptan, nelfinavir, nicotine, nifedipine, nimorazole, nizatidine, norfloxacin, ofloxacin, omeprazole, perchlorperazine, phenbenzamine, physostigmine, pizotifen, pseudoephedrine, quetiapine, quinidine, raloxifene, ranitidine, remifentanil, repaglinide, rifabutin, rifampin, rifapentine, rimantadine, ritonavir, rizatriptan, rosiglitazone, roxaditine, saquinavir, sibutramine, sildenafil, stavudine, sumatriptan, tacrine, tamoxifen, tamsulosin, terazosin, terbinafine, tinidazole, tizanidine, tolterodine, topotecan, toremifene, tramadol, trovafloxacin, vancomycin, vinblastine, vincristine, vinorelbine, vitamin $K_5$, vitamin $K_6$, vitamin $K_7$, zafirlukast, zolmitriptan, zolpidem, and pharmaceutically acceptable salts thereof.

14. The pharmaceutical composition of claim 13, wherein the hydrophobic therapeutic agent is selected from the group consisting of amlodipine, astemizole, brompheniramine, bupropion, carbinoxamine, cetrizine, cimetidine, cisapride, clemastine, clemizole, dihydroergotamine, diphenhydramine, diphenylimidazole, diphenylpyraline, domperidone, eperisone, famotidine, fexofenadine, frovatriptan, granisetron, itraconazole, ketoconazole, ketotifen, lanosprazole, leflunomide, loperamide, loratadine, methysergide, miglitol, montelukast, naratriptan, nizatidine, omeprazole, ondansetron, phenbenzamine, pseudoephedrine, raloxifene, ranitidine, repaglinide, rifabutin, rimantadine, ritonavir, rizatriptan, rosiglitazone, roxaditine, saquinavir, sibutramine, sildenafil, sumatriptan, tamsulosin, terbinafine, tizanidine, tramadol, trovafloxacin, vitamin $K_5$, vitamin $K_6$, vitamin $K_7$, zafirlukast, zolmitriptan, zolpidem, and pharmaceutically acceptable salts thereof.

15. The pharmaceutical composition of claim 9, wherein the acid is a pharmaceutically acceptable inorganic acid.

16. The pharmaceutical composition of claim 15, wherein the inorganic acid is selected from the group consisting of hydrochloric acid, hydrobromic acid, hydriodic acid, sulfiric acid, carbonic acid, nitric acid boric acid and phosphoric acid.

17. The pharmaceutical composition of claim 9, wherein the acid is a pharmaceutically acceptable organic acid.

18. The pharmaceutical composition of claim 17, wherein the organic acid is selected from the group consisting of acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and mixtures thereof.

19. The pharmaceutical composition of claim 1, wherein the hydrophobic therapeutic agent is present in an amount that is solubilized by the carrier.

20. The pharmaceutical composition of claim 1, wherein the hydrophobic therapeutic agent is present in a first amount that is solubilized by the carrier and a second amount that is suspended but not solubilized in the carrier.

21. The pharmacetical composition of claim 1, wherein the surfactant is a hydropililic surfactant selected from the group consisting of non-ionic hydrophilic surfactants having an HLB value greater than equal to about 10, ionic hydrophilie surfactants, and mixtures thereof.

22. The pharmaceutical composition of claim 21, wherein the hydrophilic surfactant is a non-ionic hydrophilic surfactant having an HLB value greater than or equal to about 10.

23. The pharmaceutical composition of claim 22, wherein the non-ionic hydrophilic surfactant is selected from the group consisting of: alkylgluceosides; alkylmaltosides; alkylthioglucosides; lauryl macrogolglycenides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid csters; polyoxyethylene glycerides; polyoxyethylene sterols and analogues thereof; polyoxyethylene vegetable oils, polyoxyethylene hydrogenated vegetable oils; reaction mixtures of polyols and at least one member selected from the group consisting of fatty acids, glycerides, vegetable oils, hydrogenated vegetable oils, in sterols; sugar esters, sugar ethers; sucroglycerides; and mixtures thereof.

24. The pharmaceutical composition of claim 22, wherein the non-ionic hydrophilic surfactant is selected from the group consisting of polyoxyethylene alkylethers; polyethylene glycol fatty acids csters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; polyoxyethylene hydrogenated vegetable oils; reaction mixtures of polyols and at least one member selected front the group consisting of fatty acids, glycerides, vegetable oil hydrogenated vegetable oils, and sterols; and mixtures thereof.

25. The pharmaceutical composition of claim 16, wherein the reaction mixture comprises a transcstcrification product of a polyol and at least one member selected from the group consisting of fatty acids, glycerides, vegetable oils, hydrogenated vegetable oils, and sterols.

26. The pharmaceutical composition of claim 25, wherein the polyol is glycerol, ethylene glycol, polyethylene glycol, sorbitol, propylene glycol, pentaerythritol or a mixture thereof.

27. The pharmaceutical composition of claim 22, wherein the non-ionic hydropililic surfactant is selected from the group consisting of PEG-10 laurate, PEG-12 laurate, PEG-20 laurate, PEG-32 laurate, PEG-32 dilaurate, PEG-12 oleate, PEG-15 olcatc, PEG-20 olcatc, PEG-20 dioleate, PEG-32 oleate, PEG-200 oleate, PEG-400 oleate, PEG-15 stearate, PEG-32 distearate, PEG-40 stearate, PEG-100 stearate, 20 dilaurate, PEG-25 glyceryl trioleate, PEG-32 dioleate, PEG-20 glyceryl laurate, PEG-30 glyceryl laurate, 20 glyceryl stearate, PEG-20 glycidyl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorl itaii oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 olcatc, Tween 40, Tween 60, sucrose monostearate, sucrose monolaurate, sucrose monopalmitate, PEG 10-100 lionyl phenol series, PEG 15-100 octyl phenol series, apoloxamcr, and mixtures thereof.

28. The pharmaceutical composition of claim 22, wherein the non-ionic hydrophilic surfactant is selected from the group consisting of PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-10 laurate, PEG-6 caprate/caprylate glycerides, PEG-8 caprate/caprylate glycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate, a poloxamer, and mixtures thereof.

29. The pharmaceutical composition of claim 22, wherein the non-ionic hydrophilic surfactant is selected from the group consisting or PEG-35 castor oil, PEG-40 hydrogenated castor oil, PEG-60 corn oil, PEG-25 glyceryl trioleate, PEG-6 caprate/caprylate glycerides, PEG-8 caprate/caprylate glycerides, polysorbate 20, polysorbate 80, tocopheryl PEG-1000 succinate, PEG-24 cholesterol, a poloxamer, and mixtures thereof.

30. The pharmaceutical composition of claim 21, wherein the hydrophilic surfactant is an ionic surfactant.

31. The pharmaceutical composition of claim 30, wherein the ionic surfactant is selected from the group consisting of fatty acid salts, bile salts, phospholipids, phosphoric acid esters, carboxylates, sulfates, sulfonates, and mixtures thereof.

32. The pharmaceutical composition of claim 21, wherein the hydrophilic surfactant is a mixture of at least one ionic surfactant and at least one non-ionic hydrophilic surfactant.

33. The pharmaceutical composition of claim 1, wherein the surfactant is a hydrophobic surfactant or mixture of hydrophobic surfactants having an HLB value of less than about 10.

34. The pharmaceutical composition of claim 33, wherein the hydrophobic surfactant is selected from the group consisting of: alcohols; polyoxymethylene alkylethers; polyglyceryl fatty acid esters, fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid conjugates of mono- and diglycerides; propylene glycol diglycerides; sorbitan fatty acid esters; polyoxyethylene sorbitan fatty acid esters; polyoxyethylene-polyoxypropylene block copolymers; transesteriefcd vegetable oils; sterols; sugar esters; sugar ethers; sucroglycerides; polyoxyethylene vegetable oils; polyoxyethylene hydrogenated vegetable oils; reaction mixtures of polyols and at least one member selected from the group consisting of fatty acids, glycerides, vegetable oils, hydrogenated vegetable oils, and sterols; and mixtures thereof.

35. The pharmaceutical composition of claim 33, wherein the hydrophobic surfactant is selected from the group consisting of fatty acids; lower alcohol fatty acid esters; polyethylene glycol glycerol fatty acid esters, polypropylene glycol fatty acid esters; polyoxyethylene glycerides; glycerol fatty acid esters; acetylated glycerol fatty acid esters; polyglyceryl fatty acid esters; lactic acid conjugates of mono- and diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; reaction mixtures of polyols and at least one member selected from the group consisting of fatty acids, glycerides, vegetable oils, hydrogenated vegetable oils, and sterols; and mixtures thereof.

36. The pharmaceutical composition of claim 33, wherein the hydrophobic surfactant is selected from the group consisting of lower alcohol fatty acids esters; polypropylene glycol fatty acid esters; propylene glycol fatty acid esters; glycerol fatty acid esters; polyglyceryl fatty acid esters; acetylated glycerol fatty acid esters; lactic acid conjugates of mono- and diglycerides; sorbitan fatty acid esters; polyoxyethylene vegetable oils; and mixtures thereof.

37. The pharmaceutical composition of claim 33, wherein the hydrophobic surfactant is selected from the group consisting of a glycerol fatty acid ester, a polyglyceryl fatty acid ester, an acetylated glycerol fatty acid ester, and mixtures thereof.

38. The pharmaceutical composition of claim 37, wherein the glycerol fatty acid ester is selected from the group consisting of a monoglyceride, a diglyceride, and mixtures thereof.

39. The pharmaceutical composition of claim 38, wherein the fatty acid of the glycerol fatty acid ester is selected from the group consisting of $C_6$ to $C_{20}$ fatty and mixtures thereof.

40. The pharmaceutical composition of claim 33, wherein the hydrophobic surfactant comprises a reaction mixture of a polyol and at least one member selected from the group consisting of fatty acids, glycerides, vegetable oils, hydrogenated vegetable oils, and sterols.

41. The pharmaceutical composition of claim 40, wherein the reaction mixture comprises a transesterification product of a polyol and at least one member selected from the group consisting of fatty acids, glycerides, vegetable oils, hydrogenated vegetable oils, and sterols.

42. The pharmaceutical composition of claim 41, wherein the polyol is selected from the group consisting of polyethylene glycol, sorbitol, propylene glycol, pentaerythritol and mixtures thereof.

43. The pharmaceutical composition of claim 33, wherein the hydrophobic surfactant is selected from the group consisting of myristic acid; oleic acid; lauric acid; stearic acid; palmitic acid; PEG 1-4 stearate; PEG 2-4 oleate; PEG-4 dilaurate; PEG-4 dioleate; PEG-4 distearate; PEG-6 dioleate; PEG-6 distearate; PEG-8 dioleate; PEG 3-16 castor oil; PEG 5-10 hydrogenated castor oil; PEG 6-20 corn oil; PEG 6-20 almond oil; PEG-6 olive oil; PEG-6 peanut oil; PEG-6 palm kernel oil; PEG-6 hydrogenated palm kernel oil; PEG-4 capric/caprylic triglyceride, mono, di, tri, tetra esters of vegetable oil and sorbitol; pentaerythritol di, tetra stearate, isostearate, oleate, caprylatc, or caprate; polyglyceryl 2-4 oleate, stearate, or isostearate; polyglyceryl 4-10 pentaoleate; polyglyceryl-3 dioleate; polyglyceryl-6 dioleate; polyglyceryl-10 trioleate; polyglyceryl-3 distearate; propylene glycol mono- or diesters of a $C_6$ to $C_{20}$ fatty acid; monoglycerides of a $C_6$ to $C_{10}$ fatty acid; acetylated monoglycerides of $C_6$ to $C_{20}$ fatty acid; diglycerides of $C_6$ to $C_{20}$ fatty acids; lactic acid conjugates of monoglycerides; lactic acid conjugates of diglycerides; cholesterol; phytosterol; PEG 5-20 soya sterol; PEG-6 sorbitan tetra, hexastearate; PEG-6 sorbitan tetraoleate; sorbitan monolaurate; sorbitan monopalmitate; sorbitan mono, trioleate; sorbitan mono, tristearate; sorbitan monoisostearate; sorbitan sesquioleate; sorbitan sesquistearate; PEG 2-5 oleyl ether; POE 2-4 lauryl ether; PEG-2 cetyl ether; PEG-2 stearyl ether; sucrose distearate; sucrose dipalmitate; ethyl oleate; isopropyl myristate; isopropyl palmitate; ethyl linoleate; isopropyl linoleate; poloxamers; and mixtures thereof.

44. The pharmaceutical composition of claim 34, wherein the hydrophobic surfactant is selected from the group consisting of oleic acid; lauric acid; glyceryl monocaprate; glyceryl monocaprylate; glyceryl monolaurate; glyceryl monooleate; glyceryl dicaprate; glyceryl dicaprylate; glyceryl dilaurate; glyceryl dioleate; acetylated monoglycerides; propylene glycol oleate; propylene glycol laurate; polyglyceryl-3 oleate; polyglyceryl-6 dioleate; PEG-6 corn oil; PEG-20 corn oil; PEG-20 almond oil; sorbitan monooleate; sorbitan monolaurate; POE-4 lauryl ether; POE-3 oleyl ether; ethyl oleate; poloxamers; and mixtures thereof.

45. The pharmaceutical composition of claim 1, wherein the triglyceride is selected from the group consisting of a pharmaceutically acceptable oil, a hydrogenated oil, a partially hydrogenated oil, a medium chain triglyceride, a long chain triglyceride, a structured triglyceride, and mixtures thereof.

46. The pharmaceutical composition of claim 1, which further comprises a solubilizer.

47. The pharmaceutical composition of claim 46, wherein the solubilizer is selected from the group consisting of alcohols, polyols, amides, esters, propylene glycol ethers and mixtures thereof.

48. The pharmaceutical composition of claim 47, wherein the alcohol or polyol is selected from the group consisting of ethanol, isopropanol, butanol, benzyl alcohol, ethylene glycol, propylene glycol, butanediols and isomers thereof, glyccrol, pentaerythritol, sorbitol, transcutol, mannitol, dimethyl isosorbide, polyethylene glycol, polypropylene glycol, polyvinylalcohol, hydroxypropyl methylcellulose, maltodextrins, cyclodextrins, and mixtures thereof.

49. The pharmaceutical composition of claim 47, wherein the amide is selected from the group consisting of 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, polyvinylpyrrolidone, and mixtures thereof.

50. The pharmaceutical composition of claim 47, wherein the ester is selected from the group consisting of ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δvalerolactone and isomers thereof, βbutyrolactone and isomers thereof, and mixtures thereof.

51. The pharmaceutical composition of claim 46, wherein the solubilizer is selected from the group consisting of ethanol, isopropanol, butanol, benzyl alcohol, ethylene glycol, propylene glycol, butanediol and isomers thereof, glycerol, pentaerythritol, sorbitol, transcutol, mannitol, dimethyl isosorbide, polyethylene glycol, polypropylene glycol, polyvinylalcohol, hydroxypropyl methylcellulose, maltodextrins, cyclodextrins, ethyl propionate, tributylcitrate, acetyl triethylcitrate, acetyl tributyl citrate, triethylcitrate, ethyl oleate, ethyl caprylate, ethyl butyrate, triacetin, propylene glycol diacetate, εcaprolactone and isomers thereof, δ-valerolactone and isomers thereof, β-butyrolactone and isomers thereof, 2-pyrrolidone, 2-piperidone, ε-caprolactam, N-methylpyrrolidone, N-ethylpyrrolidone, N-hydroxyethyl pyrrolidone, N-octylpyrrolidone, N-laurylpyrrolidone, dimethylacetamide, polyvinylpyrrolidone, glycofurol, methoxy PEG, and mixtures thereof.

52. The pharmaceutical composition of claim 46, wherein the solubilizer is selected from the group consisting of ethanol, isopropanol, benzyl alcohol, ethylene glycol, propylene glycol, 1,3-butanediol, glycerol, pentaerythritol, sorbitol, transcutol, glycofurol, dimethyl isosorbide, polyethylene glycol, polyvinylalcohol, hydroxypropyl methylcellulose, methylcellulose, ethylcellulose, hydroxypropylcyclodextrins, sulfobutyl ether conjugates of cyclodextrins, ethyl propionate, tributylcitrate, triethylcitrate, ethyl oleate, ethyl caprylate, triacetin, β-butyrolactone and isomers thereof, 2-pyrrolidone, N-methylpyrrolidinone, N-ethylpyrrolidone, N-hydroxyalkylpyrrolidone, N-octylpyrrolidone, N-laurylpyrrolidone, dimethylacetamide, polyvinylpyrrolidone, and mixtures thereof.

53. The pharmaceutical composition of claim 46, wherein the solubilizer is selected from the group consisting of triacetin, triethylcitrate, ethyl oleate, ethyl caprylate, dimethylacetamide, N-methylpyrrolidone, N-hydroxyalkylpyrrolidone, polyvinylpyrrolidone, hydroxypropyl methylcellulose, hydroxypropyl cyclodextrins, ethanol, polyethylene glycol 200-600, transcutol, glycofurol, propylene glycol, dimethyl isosorbide, and mixtures thereof.

54. The pharmaceutical composition of claim 46, wherein the solubilizer is selected from the group consisting of triacetin, ethanol, polyethylene glycol 400, glycofurol, propylene glycol and mixtures thereof.

55. The pharmaceutical composition of claim 1, wherein the ionizing agent is present in a pre-reaction amount of greater than about 1.5 mole equivalents per mole of the at least one ionizable functional group.

56. The pharmaceutical composition of claim 55, which further comprises a neutralizing agent capable of neutralizing a portion of the ionizing agent.

57. The pharmaceutical composition of claim 56, wherein the at least one ionizable functional group is an acidic functional group, the ionizing agent is a pharmaceutically acceptable base, and the neutralizing agent is a pharmaceutically acceptable acid.

58. The pharmaceutical composition of claim 56, wherein the at least one ionizable functional group is a basic functional group, the ionizing agent is a pharmaceutically acceptable acid, and the neutralizing agent is a pharmaceutically acceptable base.

59. The pharmaceutical composition of claim 56, wherein the neutralizing agent is present in an amount sufficient to neutralize the ionizing agent so that any non-neutralized ionizing agent is less than 1.5 mole equivalents per mole of the at least one ionizable functional group.

60. The pharmaceutical composition of claim 59, wherein the amount of the neutralizing agent is sufficient to neutralize the ionizing agent so that any non-neutralized ionizing agent is less than about 1.0 mole equivalents per mole of the at least one ionizable functional group.

61. The pharmaceutical composition of claim 1, wherein the ionizing agent is present in an amount of greater than about 1.0 mole equivalents per mole of ionizable functional group.

62. The pharmaceutical composition of claim 1, wherein the ionizing agent is present in an amount of about 0.1 to about 1.5 mole equivalents per mole of ionizable functional group.

63. The pharmaceutical composition of claim 1, wherein the ionizing agent is present in an amount of about 0.1 to about 1.0 mole equivalents per mole of ionizable functional group.

64. The pharmaceutical composition of claim 1, which further comprises an additive selected from the group consisting of an antioxidant, a preservative, a chelating agent, a viscomodulator, a tonicifier, a flavorant, a colorant, an odorant, an opacifier, a suspending agent, a binder, and mixtures thereof.

65. The pharmaceutical composition of claim 1 having a form selected from the group consisting of a preconcentrate, a diluted preconcentrate, a semi-solid dispersion, a solid dispersion, and a sprayable solution.

66. A dosage form comprising a capsule filled with the pharmaceutical composition of claim 1.

67. A dosage form comprising a capsule filled with the pharmaceutical composition of claim 59.

68. A dosage form comprising a capsule filled with the pharmaceutical composition of claim 60.

69. A dosage form comprising a solid particulate carrier coated with or formed from the pharmaceutical composition of claim 1.

70. A dosage form comprising the pharmaceutical composition of claim 1 formulated as a solution, a cream, a lotion, an ointment, a suppository, a spray, an aerosol, a paste or a gel.

71. The dosage form of claim 66, wherein the capsule is selected from the group consisting of a hard gelatin capsule, a soft gelatin capsule, and a starch capsule, and is optionally enteric coated.

72. The pharmaceutical composition of claim 1, which further comprises water or an aqueous solution.

73. A pharmaceutical composition comprising:
(a) a hydrophobic therapeutic agent having at least one ionizable functional group and an intrinsic water solubility of less than about 1% by weight; and (b) a carrier comprising:
  (i) an ionizing agent capable of ionizing the at least one ionizable functional group and present in an amount of greater than about 1.5 mole equivalents per mole of the at least one ionizable functional group; and
  (ii) a surfactant selected from the group consisting of nonionic hydrophilic surfactants having an HLB value greater than or equal to about 10, ionic hydrophilic surfactants, hydrophobic surfactants having an HLB value less than 10, and mixtures thereof.

74. The pharmaceutical composition of claim 73, which further comprises a neutralizing agent capable of neutralizing a portion of the ionizing agent.

75. The pharmaceutical composition of claim 74, wherein the at least one ionizable functional group is an acidic functional group, the ionizing agent is a pharmaceutically acceptable base, and the neutralizing agent is a pharmaceutically acceptable acid.

76. The pharmaceutical composition of claim 74, wherein the at least one ionizable functional group is a basic functional group, the ionizing agent is a pharmaceutically acceptable acid, and the neutralizing agent is a pharmaceutically acceptable base.

77. The pharmaceutical composition of claim 74, wherein the neutralizing agent is present in an amount sufficient to neutralize the ionizing agent so that any non-neutralized ionizing agent is less than 1.5 mole equivalents per mole of the at least one ionizable functional group.

78. The pharmaceutical composition of claim 77, wherein the amount of the neutralizing agent is sufficient to neutralize the ionizing agent so that any non-neutralized ionizing agent is less than about 1.0 mole equivalents per mole of the at least one ionizable functional group.

79. A dosage form comprising a capsule filled with the pharmaceutical composition of claim 77.

80. A dosage form comprising a capsule filled with the pharmaceutical composition of claim 78.

81. The dosage form of claim 79, wherein the capsule is a hard gelatin capsule, a soft gelatin capsule, a starch capsule or an enteric coated capsule.

82. The pharmaceutical composition of claim 73, which further comprises water or an aqueous solution.

83. The pharmaceutical composition of claim 73, which further comprises a solubilizer.

84. A pharmaceutical composition comprising:
  (a) a hydrophobic therapeutic agent having at least one ionizable functional group and an intrinsic water solubility of less than about 1% by weight; and
  (b) a carrier comprising:
    (i) an ionizing agent capable of ionizing the at least one ionizable functional group, wherein the ionizing agent is present in an amount of at least about 0.1 mole equivalents per mole of the at least one functional group;
    (ii) a surfactant selected from the group consisting of alkylglucosides; alkylmaltosides; alkylthioglucosides; lauryl macrogolglycerides; polyoxyalkylene alkyl ethers; fatty acids; lower alcohol fatty acid esters, polyoxyethylene, alkylphenols; polyethylene glycol fatty acids esters; polypropylene glycol fatty acid esters; glycerol fatty acid esters; acetylated glycerol fatty acid esters; polyethylene glycol glycerol fatty acid esters; polyglyceryl fatty acid esters; polyoxyethylene glycerides; polyoxyethylene sterols and analogues thereof; polyoxyethylene vegetable oils; polyoxyethylene hydrogenated vegetable oils; reaction mixtures of polyols and at least one member selected from the group consisting of fatty acids, vegetable oils, hydrogenated vegetable oils, and sterols; sugar esters, sugar others; sucroglycerides; fatty acid salts; bile salts; phospholipids; phosphoric acid esters; carboxylates; sulfates: and sulfonates; and
    (iii) a solubilizer present in an amount of greater than about 10% by weight, based on the total weight of the composition.

85. The pharmaceutical composition of claim 84, wherein the solubilizer is selected from the group consisting of alcohols, polyols, amides, esters, propylene glycol ethers and mixtures thereof.

86. The pharmaceutical composition of claim 84, wherein the solubilizer is selected from the group consisting of ethanol, isopropanol, butanol, benzyl alcohol, ethylene glycol, propylene glycol, butanediol and isomers thereof, glycerol, pentaerythritol, sorbitol, mannitol, dimethyl isosorbide, polyethylene glycol, polypropylene glycol, polyvinylalcohol, hydroxypropyl methylcellulose, cyclodextrins, cyclodextrins, ethyl propionate, tributylcitrate, acetyl triethylcitrate, acetyl tributyl citrate, triethylcitrate, ethyl oleate, ethyl caprylate, ethyl butyrate, triacetin, propylene glycol diacetate, ε-caprolactone and isomers thereof, δ-valerolactone and isomers thereof, β-butyrolactone and isomers thereof, 2-pyrrolidone, 2-piperidone, ε-caprolactam, N-methylpyrrolidone, N-ethylpyrrolidone, N-hydroxyethyl pyrrolidone, N-octylpyrrolidone, N-laurylpyrrolidone, dimethylacetamide, polyvinylpyrrolidone, glycofurol, methoxy PEG, and mixtures thereof.

87. The pharmaceutical composition of claim 84, wherein the solubilizer is present in an amount of at least about 15% by weight, based on the total weight of the composition.

88. The pharmaceutical composition of claim 84, wherein the ionizing agent is present in an amount of greater than about 1.5 mole equivalents per mole of ionizable functional group.

89. The pharmaceutical composition of claim 84, wherein the ionizing agent is present in an amount of greater than about 1.0 mole equivalents per mole of ionizable functional group.

90. The pharmaceutical composition of claim 84, wherein the ionizing agent is present in an amount of about 0.1 to about 1.5 mole equivalents per mole of ionizable functional group.

91. The pharmaceutical composition of claim 84, wherein the ionizing agent is present in an amount of about 0.1 to about 1.0 mole equivalents per mole of ionizable functional group.

92. A dosage form comprising a capsule filled with the pharmaceutical composition of claim 90.

93. A dosage form comprising a capsule filled with the pharmaceutical composition of claim 91.

94. A pharmaceutical composition comprising:
  (a) a hydrophobic therapeutic agent having at least one ionizable functional group and an intrinsic water solubility of less than about 1% by weight; and
  (b) a carrier comprising:
    (i) an ionizing agent capable of ionizing the at least one ionizable functional group, wherein the ionizing agent is present in an amount of at least about 0.1 mole equivalents per mole of the at least one functional group;
    (ii) a surfactant selected from the group consisting of alkylglucosides; alkylmaltosides; alkylthioglucosides; lauryl macrogolglycerides; fatty acids; lower alcohol fatty acid esters; polyoxyethylene alkylphenols; polyethylene glycol fatty acids esters; polypropylene glycol fatty acid esters; glycerol fatty acid esters; acetylated glycerol fatty acid esters; polyethylene glycol glycerol fatty acid esters; polyglyceryl fatty acid esters; polyoxyethylene sorbitan fatty acid esters; polyoxyethylene glycerides; polyoxyethylene sterols and analogues thereof, polyoxyethylene vegetable oils; polyoxyethylene hydrogenated vegetable oils; reaction mixtures of polyols and at least one member selected from the group consisting of fatty acids, vegetable oils, hydrogenated vegetable oils, and sterols; sugar esters; sugar ethers; sucroglycerides; fatty acid salts; bile salts; phospholipids; phosphoric acid esters; carboxylates; sulfates; and sulfonates; and (iii) a solubilizer comprising at least one compound selected from the group consisting of alcohols, polyols, amides, esters, and propylene glycol ethers, the alcohol or polyol being selected from the group consisting of ethanol, isopropanol, butanol, benzyl alcohol, ethylene glycol, propylene glycol, butanediols and isomers thereof, glycerol, pentaerythritol, sorbitol, mannitol, dimethyl isosorbide, polypropylene glycol, polyvinylalcohol, hydroxypropyl methylcellulose, maltodextrins, and cyclodextrins.

95. The pharmaceutical composition of claim 94, wherein the ionizing agent is present in a pre-reaction amount of greater than about 1.5 mole equivalents per mole of ionizable functional group.

96. The pharmaceutical composition of claim 94, wherein the ionizing agent is present in a an amount of greater than about 1.0 mole equivalents per mole of ionizable functional group.

97. The pharmaceutical composition of claim 94, wherein the ionizing agent is present in an amount of about 0.1 to about 1.5 mole equivalents per mole of ionizable functional group.

98. The pharmaceutical composition of claim 94, wherein the ionizing agent is present in an amount of about 0.1 to about 1.0 mole equivalents per mole of ionizable functional group.

99. A dosage form comprising a capsule filled with the pharmaceutical composition of claim 97.

100. A dosage form comprising a capsule filled with the pharmaceutical composition of claim 98.

101. A method of preparing a pharmaceutical composition of an ionizable hydrophobic therapeutic agent, the method comprising (I) providing a pharmaceutical composition comprising;
  (a) a hydrophobic therapeutic agent having at least one ionizable functional group and an intrinsic water solubility of less than about 1% by weight; and
  (b) a carrier comprising:
    (i) an ionizing agent capable or ionizing the at least one ionizable functional group, and
    (ii) a surfactant selected from the group consisting of nonionic hydrophilic surfactants having an HLB value greater than or equal to about 10, ionic hydrophilic surfactants, hydrophobic surfactants having an HLB value less than 10, and mixtures thereof; and
(II) providing a neutralizing agent in an amount sufficient to neutralize at least a fraction of the ionizing agent, wherein the non-neutralized fraction of the ionizing agent is present in an mount of at least about 0.1 mole equivalents per mole of the at least one functional group.

102. The method of claim 101, wherein the ionizing agent is present in the carrier in an amount of greater than about 1.5 mole equivalents per mole of ionizable functional group.

103. The method of claim 102, wherein the neutralizing agent is present in an amount sufficient to neutralize the ionizing agent so that any non-neutralized ionizing agent is less than 1.5 mole equivalents per mole of the at least one ionizable functional group.

104. The method of claim 103, wherein the amount of the neutralizing agent is sufficient to neutralize the ionizing agent so that any non-neutralized ionizing agent is less than about 1.0 mole equivalents per mole of the at least one ionizable functional group.

105. A method of treating an animal with an ionizable hydrophobic therapeutic agent, the method comprising:

(I) providing a dosage form of a pharmaceutical composition comprising:
  (a) a hydrophobic therapeutic agent having at least one ionizable functional group and an intrinsic water solubility of less than about 1% by weight; and
  (b) a carrier comprising:
    (i) an ionizing agent capable of ionizing the at least one ionizable functional group, wherein the ionizing agent is present in an amount of at least about 0.1 mole equivalents per mole of the at least one functional group; and
    (ii) a surfactant selected from the group consisting of nonionic hydrophilic surfactants having an HLB value greater than or equal about 10, ionic hydrophilic surfactant, hydrophobic surfactants having an HLB value less than 10, and mixtures thereof; and (II) administering said dosage form to said animal.

106. The method of claim 105, wherein the pharmaceutical composition further comprises a triglyceride.

107. The method of claim 105, wherein the dosage form is selected from the group consisting of a capsule, a solution, a cream, a lotion, an ointment, a suppository, a spray, an aerosol, a paste and a gel.

108. The method of claim 105, wherein the dosage form is administered by route selected from the group consisting of oral, parenteral, topical, transdermal, ocular, pulmonary, vaginal, rectal and transmucosal.

109. The method of claim 105, wherein the animal is a mammal.

110. The method of claim 109, wherein the mammal is a human.

111. The pharmaceutical composition of claim 24, wherein the non-ionic hydrophilic surfactant is a reaction mixture of a polyol and at least one member selected from the group consisting of the group consisting of fatty acids, glycerides, vegetable oils, hydrogenated vegetable oils, and sterols.

112. The pharmaceutical composition of claim 25, wherein the reaction mixture comprises a transesterification product of a polyol and a glyceride.

113. The method of claim 105, wherein the dosage form is administered orally.

114. The pharmaceutical composition of claim 112, wherein the glyceride is a monoglyceride, diglyceride, triglyceride, or a mixture thereof.

* * * * *